(12) United States Patent
Sakagami et al.

(10) Patent No.: US 8,531,661 B2
(45) Date of Patent: Sep. 10, 2013

(54) OPTICAL DEVICE UNIT AND DETECTION APPARATUS

(75) Inventors: Yusuke Sakagami, Shiojiri (JP); Jun Amako, Matsumoto (JP)

(73) Assignee: Seiko Epson Corporation (JP)

( * ) Notice: Subject to any disclaimer, the term of this patent is extended or adjusted under 35 U.S.C. 154(b) by 84 days.

(21) Appl. No.: 13/226,781

(22) Filed: Sep. 7, 2011

(65) Prior Publication Data

US 2012/0062881 A1  Mar. 15, 2012

(30) Foreign Application Priority Data

Sep. 14, 2010  (JP) ................................. 2010-205510

(51) Int. Cl.
  *G01J 3/44*  (2006.01)

(52) U.S. Cl.
  USPC .......................................................... 356/301

(58) Field of Classification Search
  USPC ............................................ 356/301, 72–73
  See application file for complete search history.

(56) References Cited

U.S. PATENT DOCUMENTS

| | | | |
|---|---|---|---|
| 6,134,251 A | 10/2000 | Kawase et al. | |
| 6,603,783 B1 | 8/2003 | Kawase et al. | |
| 7,242,469 B2 | 7/2007 | Wang et al. | |
| 7,384,792 B1 | 6/2008 | Wang et al. | |
| 7,428,046 B2 | 9/2008 | Wang et al. | |
| 7,524,671 B2 | 4/2009 | Clarke et al. | |
| 7,599,066 B2 | 10/2009 | Fukuda | |
| 7,651,851 B2 | 1/2010 | Clarke et al. | |
| 7,688,440 B2 | 3/2010 | Clarke et al. | |
| 7,692,787 B2 | 4/2010 | Fujimaki et al. | |
| 7,790,469 B2 | 9/2010 | Wang et al. | |
| 7,812,938 B2 | 10/2010 | Guo et al. | |
| 7,892,489 B2 | 2/2011 | Wang et al. | |
| 7,956,997 B2 | 6/2011 | Wang et al. | |
| 2006/0061762 A1 | 3/2006 | Dwight et al. | |
| 2009/0086202 A1 | 4/2009 | Wang et al. | |
| 2010/0070197 A1 | 3/2010 | Wang et al. | |
| 2010/0114514 A1 | 5/2010 | Wang et al. | |
| 2010/0296086 A1 | 11/2010 | Wang et al. | |
| 2011/0011158 A1 | 1/2011 | Bodily et al. | |
| 2012/0062881 A1 | 3/2012 | Sakagami et al. | |
| 2012/0133932 A1* | 5/2012 | Henry et al. | .................. 356/301 |

FOREIGN PATENT DOCUMENTS

| | | |
|---|---|---|
| JP | 2000-356587 | 12/2000 |
| JP | 3482824 | 10/2003 |
| JP | 2006-208271 | 8/2006 |

(Continued)

OTHER PUBLICATIONS

Li, Lifeng et al., "Convergence of the Coupled-Wave Method for Metallic Lamellar Diffraction Gratings", Optical Sciences Center, University of Arizona, Optical Society of America, vol. 10, No. 6, Jun. 1993, pp. 1184-1189.

(Continued)

*Primary Examiner* — Tarifur Chowdhury
*Assistant Examiner* — Abdullahi Nur
(74) *Attorney, Agent, or Firm* — Harness, Dickey & Pierce, P.L.C.

(57) ABSTRACT

An optical device unit includes: an optical device which has an electrical conductor and is capable of enhancing Raman scattering light generated by receiving light from a light source; and a first guide unit which guides a gaseous sample to the optical device. The optical device unit is detachable from the detection apparatus.

10 Claims, 18 Drawing Sheets

(56) References Cited

FOREIGN PATENT DOCUMENTS

| | | |
|---|---|---|
| JP | 2007-010648 | 1/2007 |
| JP | 2008-529006 | 7/2008 |
| JP | 2009-250951 | 10/2009 |

OTHER PUBLICATIONS

Inoue, Masahiro et al., "Suface Enhanced Raman Scattering by Metal Spheres. I. Cluster Effect", Journal of Physical Society of Japan, vol. 52, No. 11, Nov. 1983, pp. 3853-3864.

* cited by examiner

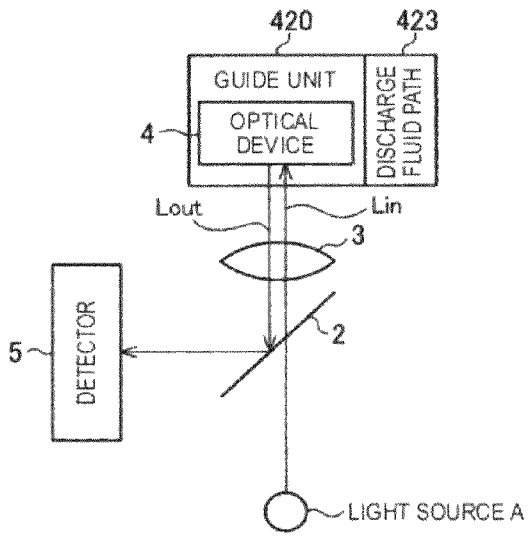
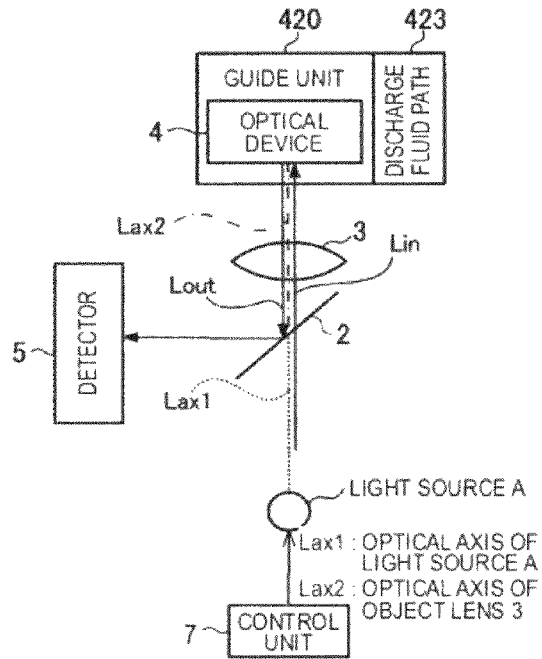
FIG. 1A
FIG. 1B
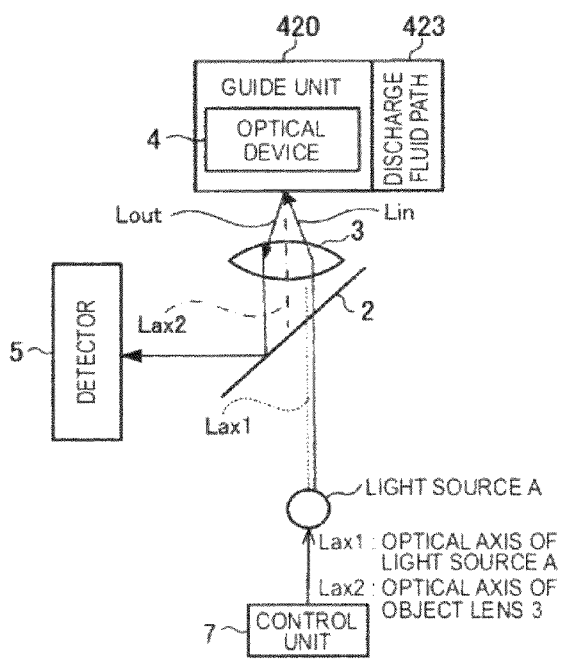
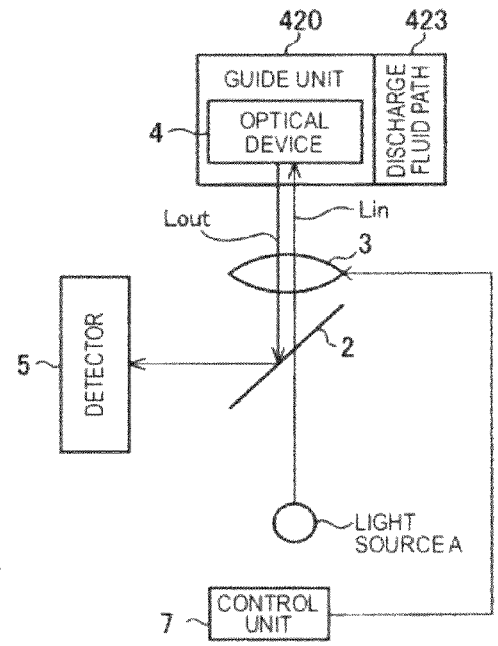
FIG. 1C
FIG. 1D

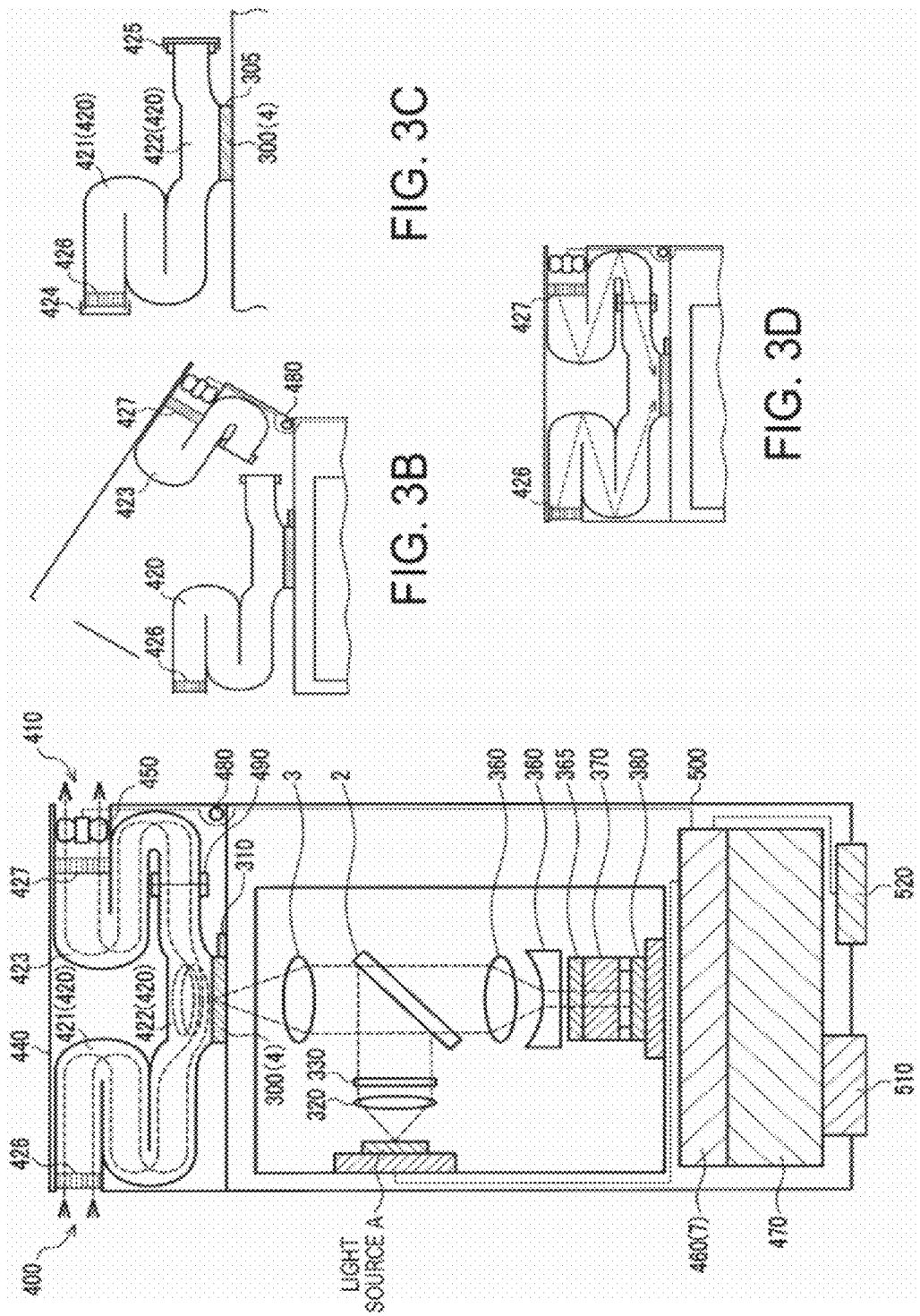

|  | STABILIZED He-Ne LASER | DPSS (Nd:YAG LASER) | STABILIZED SEMICONDUCTOR LASER | VCSEL |
|---|---|---|---|---|
| WAVELENGTH | 632 nm | 1064 / 532 nm | 785 nm | 785 nm |
| LINE WIDTH | ○ 1 GHz (~ 10 pm) | ◎ 10 kHz (~ 0.01 fm) | △ 0.03 nm | ◎ 30 MHz (~ 50 fm) |
| WAVELENGTH STABILITY | ◎ 1 MHz | △ 0.2 nm | ◎ 0.01 nm/°C | ◎ 0.06 nm/°C |
| POLARIZATION | ○ > 20 dB | ○ > 20 dB | ○ > 20 dB | ○ POLARIZATION SURFACE DIRECTION CONTROL |
| POWER CONSUMPTION (~10 mW OUTPUT) | × SEVERAL W | × SEVERAL W ~ SEVERAL TENS W | △ SEVERAL HUNDREDS mW | ◎ SEVERAL TENS mW |
| VOLUME | × 1,000 cc | × 500 ~ 1,000 cc | × 500 ~ 1,000 cc | ◎ ~1 cc |

FIG. 6

OPTICAL DEVICE UNIT AND DETECTION APPARATUS

BACKGROUND

1. Technical Field

The present invention relates to an optical device unit and a detection apparatus.

2. Related Art

In general, a Raman spectroscopic apparatus includes a detector for obtaining Raman spectra by detecting Raman scattering light depending on a detection target substance. The detection target substance can be specified by performing a spectroscopic analysis using the Raman spectra. However, the signal intensity of the Raman scattering light is typically weak, and its detection sensitivity is low.

JP-T-2008-529006 discloses a handheld Raman blood analyzer to provide surface-enhanced Raman scattering using gold colloid sol-gel/strips and increase the signal intensity of the Raman scattering light.

In addition, a localized plasmon can be generated by irradiating excitation light onto a metal surface. The electric field can be locally enhanced by combining the excitation light and the localized plasmon. It is envisaged that Raman scattering light is enhanced by the enhanced electric field in the surface-enhanced Raman scattering.

Japanese Patent No. 3482824 discloses a vertical cavity surface-emitting laser (VCSEL) capable of safely controlling a polarization surface in which excitation light can be provided using the VCSEL.

Optical absorption is generated by localized plasmon resonance when excitation light and localized plasmon are combined. For example, JP-A-2000-356587 discloses a technique of improving sensor sensitivity based on localized surface plasmon resonance using a substrate having a surface where metal micro particles are fixed. JP-A-2007-10648 discloses a localized plasmon resonance sensor having a resonance peak shifted to a long wavelength side and a resonance peak shifted to a short wavelength side. In addition, JP-A-2009-250951 discloses an electric field enhancement device including a micro resonator having a plurality of resonance areas in order to make it possible to resonate for a plurality of wavelengths.

A Raman spectroscopic apparatus typically includes an optical device having an electrical conductor such as a metal nano-structure where a detection target substance can be adsorbed. Raman scattering light caused by an enhanced electric field can be detected by guiding the target substance into the enhanced electrical field near the optical device. Depending on the type of target substance, or the type of optical device, a detection sensitivity of the Raman scattering light may be low.

SUMMARY

An advantage of some aspects of the invention is to provide an optical device unit and a detection apparatus capable of improving the detection sensitivity.

An aspect of the invention is directed to a detachable optical device unit to a detection apparatus, the optical device unit including: an optical device having an electrical conductor, the optical device being capable of enhancing Raman scattering light generated by receiving light from a light source of the detection apparatus; and a first guide unit that guides a gaseous sample to the optical device.

In the optical device unit of the aspect of the invention, the used optical device unit may be removed from the detection apparatus, and a new optical device unit may be installed in the detection apparatus. If the optical device unit is exchanged in this manner, it is possible to increase detection sensitivity of the detection apparatus while the gaseous samples attached to the first guide unit and the optical device do not influence the subsequent detection or measurement.

In the optical device unit of the aspect of the invention, the first guide unit may have a first fluid path that imports the gaseous sample from an import hole, and the first fluid path may have an inner wall surface that blocks an incident ray of external light between the import hole and the optical device.

As a result, external light rarely reaches the optical device, and a ratio of the external light (noise) with respect to the Raman scattering light (signal) decreases. Therefore, it is possible to improve a signal-to-noise ratio (S/N ratio) when the Raman scattering light is detected and increase the detection sensitivity.

The optical device unit of the aspect of the invention may further include a filter for removing dust in the air in the first fluid path, and the filter may block the external light.

As a result, dust and external light rarely arrive at the optical device due to the presence of the filter, and it is possible to increase the detection sensitivity.

The optical device unit of the aspect of the invention may further include an identification code that can be read by the detection apparatus and identifies the optical device.

As a result, the detection apparatus can recognize the type of the optical device or the gaseous sample detectable by the optical device. In a case where the detection apparatus carries out a spectroscopic analysis using Raman spectra, such a detection apparatus (Raman spectroscopic apparatus) can easily detect or specify the gaseous sample (target substance) corresponding to the optical device.

In the optical device unit of the aspect of the invention, the first guide unit may have a second fluid path connected to the first fluid path, and the second fluid path may rotate the gaseous sample in an area facing the optical device.

As a result, due to presence of the second fluid path of the guide unit, a possibility that the gaseous sample enters the optical device increases. Therefore, the signal intensity of the Raman scattering light becomes stable. For example, even when the amount of the gaseous sample is small, it is possible to easily detect or specify the gaseous sample (a target substance).

Another aspect of the invention is directed to a detection apparatus including: the optical device unit described above, a second guide unit connectable to the first guide unit; the light source; a first optical system that introduces the light from the light source into the electrical conductor of the optical device; and a detector that detects Raman scattering light from the light scattered or reflected by the electrical conductor, wherein the second guide unit guides the gaseous sample to the outlet duct.

As a result, by connecting the first guide unit of the optical device unit and the second guide unit of the detection apparatus, it is possible to provide a detection apparatus in which the optical device unit is exchangeable.

In the detection apparatus of the aspect of the invention, the electrical conductor of the optical device may include a first protrusion group having a plurality of protrusions, each of the plurality of protrusions of the first protrusion group may be arranged with a first period along a direction parallel to the virtual plane of the electrical conductor, and the first optical system introduces the light from the light source into the first protrusion group such that a component parallel to the virtual plane of a polarization direction of the light from the light source is parallel to an arrangement direction of the first protrusion group.

As a result, the enhanced electric field of the optical device can be increased by the first protrusion group. In addition, linearly-polarized light in which a component parallel to the virtual plane of the polarization direction is parallel to the arrangement direction of the first protrusion group can be incident to the optical device. As a result, propagation type surface plasmons can be excited.

In the detection apparatus of the aspect of the invention, each of the plurality of the protrusions of the first protrusion group may include a second protrusion group formed of an electrical conductor on a front surface of the first protrusion group, and each of a plurality of protrusions of the second protrusion group corresponding to any one of the plurality of protrusions of the first protrusion group may be arranged with a second period shorter than the first period along a direction parallel to the virtual plane.

As a result, the enhanced electric field in the optical device can increase also in the second protrusion group.

The detection apparatus of the aspect of the invention may further include a third protrusion group formed of a third electrical conductor on a surface between neighboring protrusions of the first protrusion group on a surface where the first protrusion group is arranged, and each of a plurality of protrusions of the third protrusion group may be arranged with a third period shorter than the first period along the direction parallel to the virtual plane between the neighboring protrusions of the first protrusion group.

As a result, the enhanced electric field in the optical device can increase also in the third protrusion group.

In the detection apparatus of the aspect of the invention, surface plasmon resonance in the event that a propagating direction of the light from the light source is inclined with respect to a normal line directed to the virtual plane may be generated in each of first and second resonance peak wavelengths, a first resonance peak wavelength band having the first resonance peak wavelength may have an excitation wavelength in surface-enhanced Raman scattering caused by the surface plasmon resonance, and a second resonance peak wavelength band having the second resonance peak wavelength may have a Raman scattering wavelength in the surface-enhanced Raman scattering.

As a result, surface plasmon resonance is generated in each of the first and second resonance peak wavelengths by the light incident to the first protrusion group in which protrusions are arranged with the first period. In this case, the incident angle of the light and the first period are set such that the first resonance peak wavelength band including the first resonance peak wavelength includes an excitation wavelength of surface-enhanced Raman scattering, and the second resonance peak wavelength band of the second resonance peak wavelength includes a Raman scattering wavelength in surface-enhanced Raman scattering. As a result, it is possible to improve an enhancement degree of the electric field in both the excitation wavelength and the Raman scattering wavelength.

The detection apparatus of the aspect of the invention may further include a second optical system that guides the Raman scattering light to the detector, and the detector may receive the Raman scattering light through the second optical system.

As a result, it is possible to efficiently receive the Raman scattering light using the second optical system.

BRIEF DESCRIPTION OF THE DRAWINGS

The invention will be described with reference to the accompanying drawings, wherein like numbers reference like elements.

FIGS. 1A to 1D illustrate a configuration example of a detection apparatus including an optical device unit according to an embodiment of the invention.

FIGS. 3A to 3D illustrate a specific configuration example of a detection apparatus including an optical device unit according to an embodiment of the invention.

FIG. 6 is an explanatory diagram illustrating characteristics of light sources.

DESCRIPTION OF EXEMPLARY EMBODIMENTS

Figure 2A:
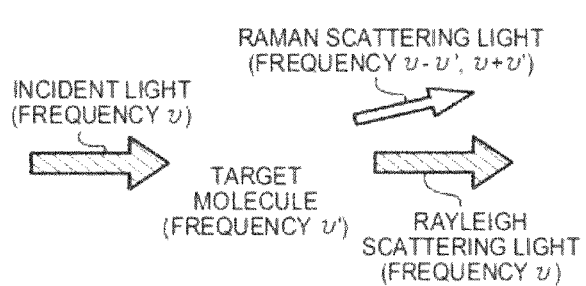
FIGS. 2A to 2E are explanatory diagrams of the principle of detecting Raman scattering light.

Hereinafter, preferable embodiments of the invention will be described in detail. Embodiments of the invention described below are not intended to limit the scope of the invention described in the claims, and all of the configurations described in the embodiments of the invention are not necessarily indispensable as solving means of the invention.

1. Overview
1.1. Basic Configuration

FIGS. 1A to 1D illustrate an exemplary configuration of a detection apparatus including an optical device unit according to an embodiment of the invention. As shown in FIG. 1A, the optical device unit includes an optical device 4 and a guide unit 420 (first guide unit), and the detection apparatus includes the optical device unit, a discharge fluid path 423 (second guide unit), a light source A, an optical system, and a detector 5. The optical device unit is detachable from the detection apparatus, and the guide unit 420 and the discharge fluid path 423 are connected thereto.

The optical system (first optical system) includes a half mirror 2 and an object lens 3. The light source A may radiate light having a predetermined polarization direction. In addition, the light source A is not limited to the example in FIG. 1A but may include a plurality of light sources. In addition, the light source A may have directivity. Preferably, the light source A may have a light source with high directivity (for example, laser).

The half mirror 2 and the object lens 3 (in the broadest sense, the optical system) introduces the light from the light source A into the electrical conductor of the optical device 4. In addition, the guide unit 420 guides the gaseous sample to the optical device 4. The discharge fluid path 423 is guided to the optical device 4 and discharges the gaseous sample. The detector 5 detects the Raman scattering light from the light scattered or reflected by the electrical conductor. The detection apparatus may be called a Raman detection apparatus, and the detection apparatus further performing a spectroscopic analysis using Raman spectra may also be called a Raman spectroscopic apparatus.

The inventors have recognized that the gaseous sample is continuously attached to the optical device 4 and the guide unit 420 used in the Raman spectroscopic apparatus, and the signal intensity of the Raman scattering light caused by the enhanced electric field in the vicinity of the electrical conductor of the optical device 4 is not stable. In this regard, it is possible to increase the detection sensitivity of the detector 5 by separating the optical device 4 and the guide unit 420 and by improving the guide unit 420 in some cases. In addition, it is possible to improve the detection sensitivity by separating the optical device 4 and the guide unit 420 from the detection apparatus. In addition, it is possible to increase a possibility that the gaseous sample enters the optical device by improving the guide unit 420. Therefore, it is possible to obtain a stable signal intensity of the Raman scattering light. The Raman scattering light and the enhanced electric field will be described below. In addition, the guide unit 420 will be described below.

In the example in FIG. 1A, the optical path of the light Lin (incident light) from the light source A and the optical path of the light Lout (scattered light, reflective light) from the optical device 4 do not accurately represent the actual optical path. In other words, they are intended to only show presence of the optical path of the light Lin (incident light) from the light source A and presence of the optical path of the light Lout (scattered light, reflective light) from the optical device 4.

In the example in FIG. 1B, the detection apparatus may include a control unit 7 that variably controls the relative position between the optical device 4 and the light source A. Specifically, the control unit 7 may change the position of the light source A. In addition, the control unit 7 may include an operation unit such as an XY stage or may only transmit a signal to the operational unit.

The control unit 7 may change the position of the optical device 4. In the example in FIG. 1B, the control unit 7 changes the position of the light source A such that the optical axis Lax1 of the light source A matches the optical axis Lax2 of the object lens 3 (in the broadest sense, the optical axis of the optical system).

In this case, in practice, it is anticipated that the light Lin from the light source A is overlapped with the optical axis Lax1 of the light source A and the optical axis Lax2 of the object lens 3. However, in the example in FIG. 1B, the light Lin from the light source A is illustrated so as not to be overlapped with the optical axis Lax1 of the light source A and the optical axis Lax2 of the object lens 3. In the example in FIG. 1B, in order to illustrate that the optical axis Lax1 of the light source A matches the optical axis Lax2 of the object lens 3, the light Lin from the light source A is illustrated so as not to be overlapped with the optical axis Lax1 of the light source A and the optical axis Lax2 of the object lens 3.

In the example in FIG. 1C, the control unit 7 changes the position of the light source A such that the optical axis Lax1 of the light source A is deviated from the optical axis Lax2 of the object lens 3. In this case, in practice, it is anticipated that the light Lin from the light source A is overlapped with the optical axis Lax1 of the light source A. However, in the example in FIG. 1C, the light Lin from the light source A is illustrated so as not to be overlapped with the optical axis Lax1 of the light source A. In the example in FIG. 1C, in order to illustrate that the optical axis Lax1 of the light source A does not match the optical axis Lax2 of the object lens 3, the light Lin from the light source A is illustrated so as not to be overlapped with the optical axis Lax1 of the light source A.

In the example in FIG. 1D, the detection apparatus may have a control unit 7 for variably controlling a relative position between the optical device 4 and the optical system. Specifically, the control unit 7 may change a position of the object lens 3. It is possible to match the optical axis of the light source A with the optical axis of the object lens 3 by changing the position of the object lens 3. Otherwise, the optical axis of the light source A may be deviated from the optical axis of the object lens.

1.2. Principle of Detection

FIGS. 2A to 2E are explanatory diagrams illustrating the principle of detection in the Raman scattering light. The example in FIG. 2A illustrates Raman spectroscopy, in which, when the incident light (frequency ν) is irradiated onto a target molecule (in the broadest sense, a target substance), a significant amount of the incident light is scattered as Rayleigh scattering light, and a frequency ν or a wavelength of the Rayleigh scattering light is not changed. A part of the incident light is scattered as Raman scattering light, and the frequency (ν−ν' and ν+ν') or the wavelength of the Raman scattering light is reflected on the frequency ν' (molecular vibration) of the target molecule. A part of the incident light is used to vibrate the target molecule to reduce energy. However, the vibration energy of the target molecule may be added to optical energy or vibration energy of the Raman scattering light. Such a shift (ν') of the frequency is called a Raman shift.

Figure 2B:
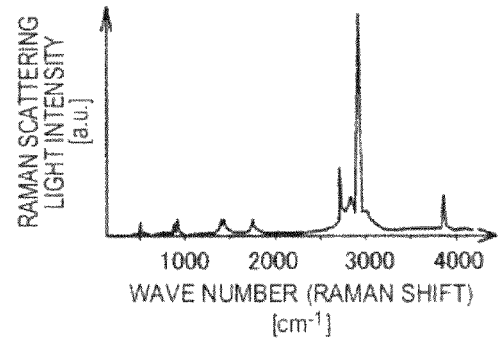

The example in FIG. 2B illustrates a Raman spectrum in a case where the target molecule is a molecule of acetaldehyde. In other words, it is possible to specify a molecule of acetaldehyde by analyzing the Raman spectrum shown in FIG. 2B. However, in a case where the amount of target molecules is small, the Raman scattering light is typically too weak to detect or specify the target molecule. In this regard, it is preferable that the Raman scattering light be enhanced by the enhanced electric field by adding the enhanced electric field. In addition, the Raman spectrum in FIG. 2B shows the Raman shift using the wave number.

Figure 2C:
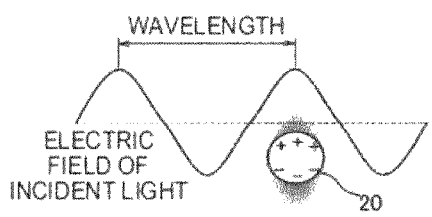

The example in FIG. 2C illustrates an enhanced electric field formed when the incident light (irradiated light) is irradiated onto the metal fine-particle 20. In a case where the incident light is irradiated onto metal fine-particles 20 (metal nano-particles) smaller than the wavelength of the incident light, the electric field of the incident light is applied to free electrons present on the surfaces of the metal fine-particles 20 to generate resonance. As a result, the electric dipole caused by the free electrons is excited within the metal fine-particles 20 so that an enhanced electric field stronger than the electric field of the incident light is formed in the vicinity of the metal fine-particles 20. Such a phenomenon is unique in electric conductors such as metal fine-particles 20 smaller than the wavelength of the incident light.

Figure 2D:
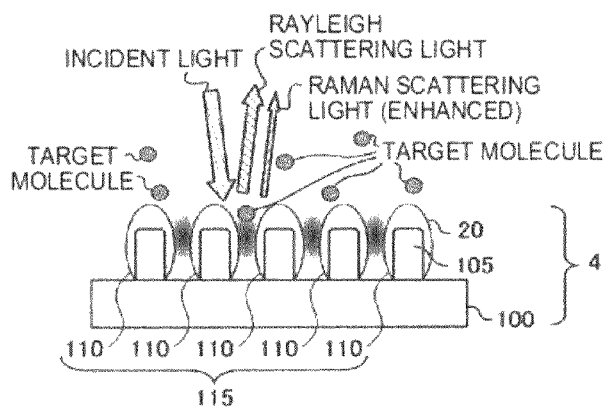

The example in FIG. 2D illustrates surface-enhanced Raman scattering (SERS) when the incident light is irradiated onto the optical device 4. The optical device 4 includes a substrate 100. It is possible to provide a protrusion group 115 (in the broadest sense, a metal nano-structure) having a plurality of protrusions 110 by forming metal fine-particles 20 in convex portions 105 of the substrate 100. It is possible to form an enhanced electric field between neighboring protrusions 110 (electrical conductors formed in the convex portions 105) of the protrusion group 115 by irradiating incident light onto such an optical device. If the target molecule enters the enhanced electric field, the Raman scattering light caused by the target molecule is enhanced by the enhanced electric field, and the signal intensity of the Raman scattering light becomes strong. In such surface-enhanced Raman scattering, it is possible to increase detection sensitivity even when the number of target molecules is insignificant.

Figure 2E:
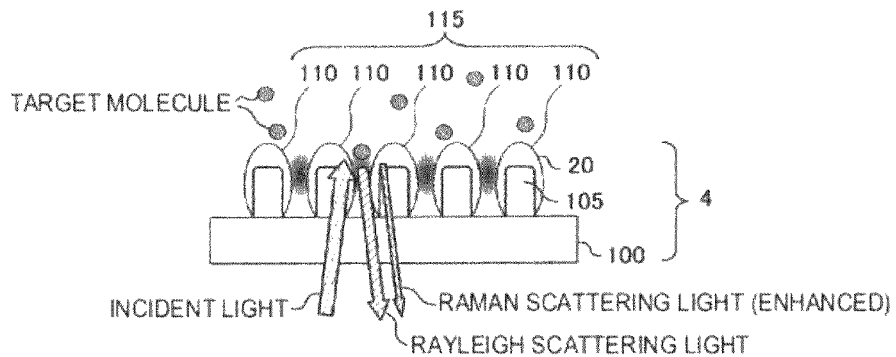

Although the incident light is irradiated from the surface side (the electrical conductor side) of the optical device 4 in the example in FIG. 2D, the incident light may be irradiated from the rear side (the substrate 100 side) of the optical device 4 as shown in FIG. 2E. In the example in FIG. 2E, it is possible to detect the Raman scattering light and the Rayleigh scattering light on the rear side of the optical device 4.

The optical device 4 illustrated in FIGS. 1A to 1D preferably has a metal nano-structure as shown in FIG. 2D. However, it may not be necessary to provide the enhanced electric field as shown in FIG. 2C.

2. Specific Example
2.1. Entire Configuration

FIGS. 3A to 3D illustrate an exemplary configuration of the detection apparatus having the optical device unit in detail according to an embodiment of the invention. In the following description, like reference numerals denote like elements as in FIG. 1, and description thereof will not be repeated. In the example in FIG. 3A, the optical device unit is integrated in the detection apparatus. In the example in FIG. 3B, the optical device unit is extracted from the detection apparatus before the optical device unit is integrated. In the example in FIG. 3C, the optical device unit for exchange is illustrated. In the example in FIG. 3D, an entrance path of the external light is illustrated. In order to increase the detection sensitivity of the detection apparatus, the optical device unit is detachably integrated in the detection apparatus. By removing the used optical device unit from the detection apparatus and installing a new optical device unit in the detection apparatus, the gaseous sample attached to the guide unit 420 and the optical device 4 does not affect the subsequent detection or measurement.

The optical device unit of the detection apparatus in FIG. 3A includes a sensor chip 300 (in the broadest sense, the optical device 4) and a guide unit 420 (transport unit). The target substance is introduced from the inlet duct 400 (loading entrance or import hole) to the inner side of the guide unit 420 (first guide unit) and the discharge fluid path 423 (second guide unit) and discharged from the outlet duct 410 to the outer side of the guide unit 420 (first guide unit) and the discharge fluid path 423 (second guide unit). In the example in FIG. 3A, the detection apparatus includes a fan 450 (in the broadest sense, suction unit) near the outlet duct 410 so that pressures within the inlet fluid path 421 (first fluid path) of the guide unit 420, the fluid path 422 (second fluid path) in an area facing the sensor chip 300, and the discharge fluid path 423 (third fluid path) are reduced as the fan 450 is operated. As a result, the target substance (gaseous sample) is imported to the guide portion 420. The target substance passes through the fluid path 422 near the sensor chip 300 via the inlet fluid path 421 and is discharged from the discharge fluid path 423. In this case, a part of the target substances are adhered to the surface of the sensor chip 300 (an electrical conductor).

The discharge fluid path 423 for guiding the gaseous sample to the outlet duct 410 may be connected to fluid path 422 (in the broadest sense, the guide unit 420) near the sensor chip 300. In the example in FIG. 3A, the discharge fluid path 423 and the fluid path 422 are connected through a connector 490 such as a flange or a coupler.

The sensor chip 300 can enhance the Raman scattering light generated by receiving the light from the light source A, and the fluid path of the guide unit 420 may be improved in order to increase a possibility that the gaseous sample is attached to or adsorbed on the surface of the sensor chip 300. In a simple fluid path (not shown), the gaseous sample may pass through the sensor chip 300. Therefore, the guide unit 420 may have a fluid path such that the gaseous sample is circulated around the vicinity of the surface of the sensor chip 300. The circulated gaseous sample is difficult to directly go to the outlet duct 410 or the discharge fluid path 423 and may stay in the fluid path 422 near the sensor chip 300.

As shown in FIG. 3A, the gaseous sample can be circulated in the fluid path 422 (the second fluid path) in the vicinity of the sensor chip 300. Due to the generation of rotating flow, the possibility in which the gaseous sample is entering the sensor chip 300 improves. Therefore, the signal intensity of the Raman scattering light becomes stable, and even in the case where the amount of the gaseous sample is small the gaseous sample (target substance) can be easily detected or specified.

As the target substance trace molecules such as a narcotic drugs, alcohol, or residual pesticides or pathogenic agents such as viruses may be envisaged.

Preferably, a possibility that the gaseous sample makes contact with the surface of the sensor chip 300 is high. Furthermore, the external light (not shown) does not reach the sensor chip 300 as long as possible. As shown in FIG. 3A, the inlet fluid path 421 (first fluid path) of the guide unit 420 may have a reflecting structure. By reducing a ratio of the external light (noise) to the Raman scattering light (signal), it is possible to improve the signal-to-noise (S/N) ratio to detect the Raman scattering light, and thus, to enhance the detection sensitivity.

If the inlet fluid path 421 is straight, it is difficult to block the external light in the inlet fluid path 421, so that the detection sensitivity may be degraded.

The example in FIG. 3D illustrates an optical path when the external light reaches the fluid path 422 in the vicinity of the sensor chip 300 through the inlet fluid path 421. For example, as shown in FIG. 3D, the external light is reflected by the inner wall of the inlet fluid path 421 three times. The inlet fluid path 421 has an inner wall surface for blocking the incident rays of the external light between the inlet duct 400 (import hole) and the sensor chip 300. Through such a reflecting structure, the inlet fluid path 421 is provided with a light-blocking property.

Although the inlet fluid path 421 has a reflecting structure in the example in FIG. 3A, the inner wall of the inlet fluid path 421 is preferably curved such that the resistance of the fluid path is reduced. In addition, the inner wall of the inlet fluid path 421 is preferably made of a material having a low light reflectance to increase the light blocking property. Furthermore, the discharge fluid path 423 (third fluid path) of the guide unit 420 also preferably has a structure capable of increasing the light blocking property.

The example in FIG. 3D illustrates an optical path (incident rays) when the external light reaches the fluid path 422 near the sensor chip 300 through the discharge fluid path 423. For example, as shown in FIG. 3D, the external light is reflected 3 times by the inner wall of the discharge fluid path 423. The discharge fluid path 423 has an inner wall surface for blocking the incident rays of the external light between the outlet duct 410 and the sensor chip 300. Through such a reflecting structure, the discharge fluid path 423 may be provided with the light blocking property.

In the example in FIG. 3A, the inlet fluid path 421 (in the broadest sense, guide unit 420, and in broadest possible sense, the optical device unit) may include a filter 426 (for example, the dust-removing filter) for removing dust in the air. The filter 426 preferably blocks the external light, and may serve as both the dust-removing filter and the light-blocking filter. In addition, the discharge fluid path 423 (in the broadest sense, the detection apparatus) may also include a filter 427 (for example, a light-blocking filter) for blocking the external light.

In the example in FIG. 3A, the detection apparatus includes a covering 440, and the covering 440 may store a sensor chip 300. In addition, the detection apparatus includes a casing 500, and the light source A, the half mirror 2, the object lens 3, and the detector 5 may be included in the casing 500. The detector 5 includes a spectroscopic element 370 and an optical receiver element 380. The spectroscopic element 370 may include etalon. Furthermore, the detection apparatus may include a condensing lens 360, an optical filter 365, a processing unit 460, a power supply unit 470, a communication connection plug 510, and a power connection plug 520.

In the example in FIG. 3A, the detection apparatus has a hinge 480, and the covering 440 can be opened/closed through the hinge 480. While the covering 440 is opened, the used optical device unit may be removed. Alternatively, as shown in FIG. 3B, while the covering 440 is opened, a new optical device unit may be integrated into the detection apparatus. In addition, the detection apparatus has a latching portion (not shown), and the optical device unit has a latched portion (not shown) corresponding to the latching portion so that the optical device unit can be positioned. In addition, the sensor chip detection element 310 may detect whether or not the sensor chip 300 (in the broadest sense, optical device unit) is suitably integrated into the detection apparatus. FIG. 3C illustrates an optical device unit for exchange, and the optical device unit may have encapsulation members 424 and 425 to prevent contamination of the guide unit 420 and the sensor chip 300. The optical device unit may have an identification code 305 (for example, a bard code) for identifying the sensor chip 300, and the sensor chip detection element 310 (for example, a barcode reader) may read the identification code 305.

In the example in FIG. 3A, the detection apparatus further includes a polarization control element 330 and a collimator lens 320 corresponding to the light source A. The light emitted from the light source A is collimated by the collimator lens 320 and plane-polarized by the polarization control element 330. In addition, if a surface-emitting laser is employed as the light source to allow the plane-polarized light to be emitted, it is possible to omit the polarization control element 330.

The light from the light source A is attracted to the direction of the sensor chip 300 by the half mirror 2 (dichroic mirror), condensed to the object lens 3, and is incident to the sensor chip 300. For example, a metal nano-structure is formed on the surface of the sensor chip 300. From the sensor chip 300 Rayleigh scattering light and Raman scattering light are emitted from the sensor chip 300 by surface-enhanced Raman scattering. The Raman scattering light and the Rayleigh scattering light from the sensor chip 300 pass through the object lens 3 and are attracted to the direction of the detector 5 by the half mirror 2.

In the example in FIG. 3A, the light from the light source A reaches the front surface of the sensor chip 300 from the rear surface thereof, and the Rayleigh scattering light and the Raman scattering light are generated from the vicinity of the metal nano-structure, so that the Rayleigh scattering light and the Raman scattering light are radiated from the rear surface of the sensor chip 300 (refer to FIG. 2E). In addition, the arrangement of the sensor chip 300 in FIG. 3 may be changed such that the light from the light source A directly reaches the front surface of the sensor chip 300 (refer to FIG. 2D).

In the example in FIG. 3A, the Rayleigh scattering light and the Raman scattering light from the sensor chip 300 are condensed by the condensing lens 360 and reach the optical filter 365. In addition, the Raman scattering light is extracted by the optical filter 365 (for example, a notch filter), and the optical receiver element 380 receives the Raman scattering light through the spectroscopic element 370. The wavelength of the light passing through the spectroscopic element 370 can be controlled (selected) by the processing unit 460.

The optical receiver element 380 receives the Raman scattering light through the optical system and the spectroscopic element 370. The optical system (second optical system) includes a half mirror 2, a condensing lens 360, and an optical filter 365. A Raman spectrum unique to the target substance is obtained by the spectroscopic element 370 and the optical receiver element 380, and the target substance can be specified by checking the obtained Raman spectrum against the previously-stored data.

In the example in FIG. 3A, the processing unit 460 may turn on/off the power of the light source A. For example, the processing unit 460 may carry out the function of the control unit 7 shown in FIG. 1B, and the processing unit 460 may variably control the position of the light source A. In addition, the processing unit 460 may send instructions to the detector 5 and the fan 450 other than the light source A shown in FIG. 3A, and the processing unit 460 may control the detector 5 and the fan 450 as well as the light source A. In addition, the processing unit 460 may carry out the spectroscopic analysis using the Raman spectrum, and the processing unit 460 may specify the target substance. In addition, the processing unit 460 may transmit the detection result of Raman scattering light, the spectroscopic analysis result of the Raman spectrum is transmitted to an external device (not shown) connected to the communication connection plug 510.

In the example in FIG. 3A, the power supply unit 470 may supply power to the light source A, the detector 5, the fan 450, the processing unit 460 shown in FIG. 3A. The power supply unit 470 may be configured using a secondary battery as well as a primary battery and an AC adaptor. In a case where the power supply unit 470 is configured using the secondary battery, an electric charger (not shown) connected to the power connection plug 520 may charge the secondary battery. In a case where the power supply unit 470 is configured using an AC adaptor, the AC adaptor is arranged in an external side of the detection apparatus and connected to the power connection plug 520. In addition, the detection apparatus may include a display unit (the display unit 540 in the example in FIG. 4), and the display unit may display the state of the power supply unit 470 (for example, out of battery, now charging, charging completed, power is being supplied).

Figure 4:
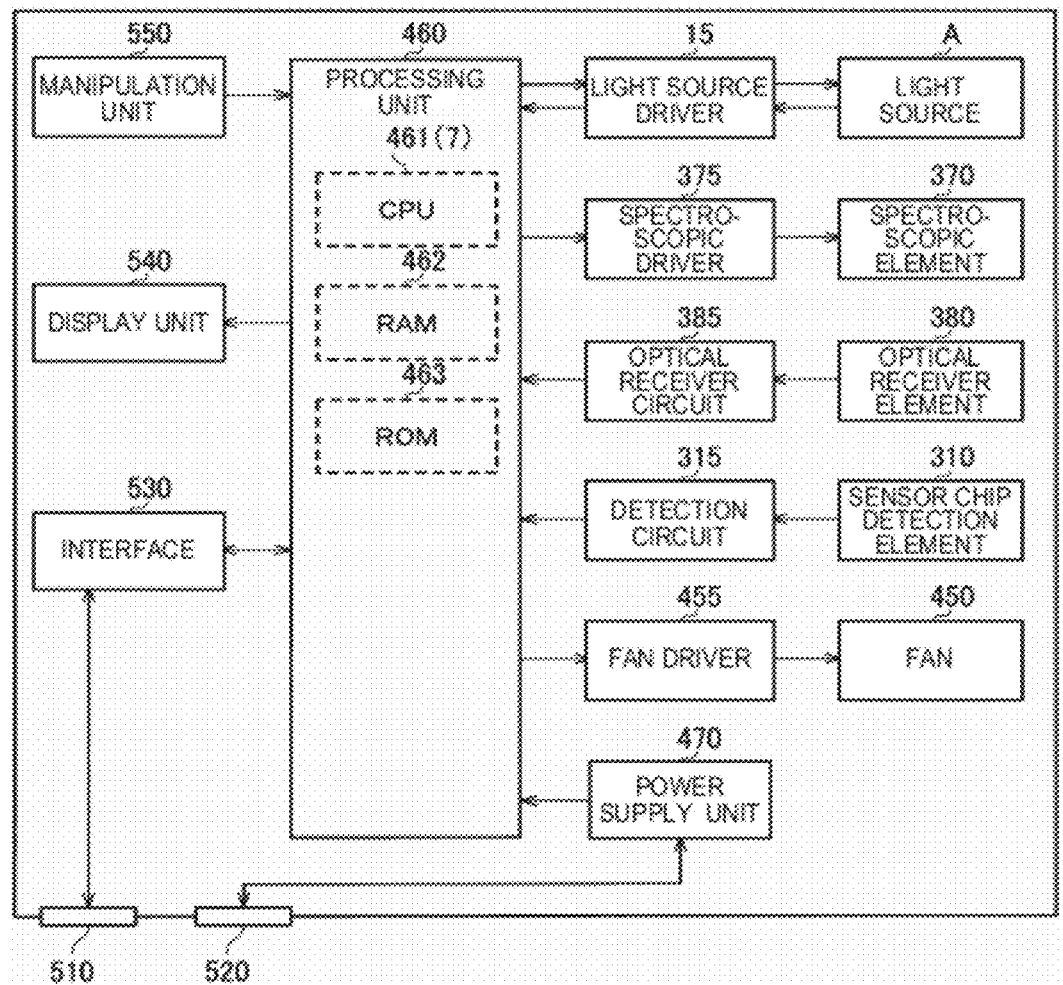
FIG. 4 is an exemplary block diagram illustrating the detection apparatus of FIG. 3A.

FIG. 4 illustrates an exemplary block diagram of the detection apparatus of FIG. 3A. In the following description, like reference numerals denote like elements as in FIG. 3A, and description thereof will not be repeated. As shown in FIG. 4, the detection apparatus may further include a display unit 540, a manipulation unit 550, and an interface 530. In addition, the processing unit 460 shown in FIG. 3A may include a central processing unit (CPU) 461, random access memory (RAM) 462, and read only memory (ROM) 463. Furthermore, the detection apparatus may include a light source driver 15, a spectroscopic driver 375, an optical receiver circuit 385, and a fan driver 455. Hereinafter, an operational example of the detection apparatus shown in FIG. 4 will be described.

In the example in FIG. 4, the CPU 461 may determine whether or not preparation to detect the Raman scattering light has been completed, and the CPU 461 may send a signal indicating that the preparation has been completed to the display unit 540. In addition, the CPU 461 may send signals other than that signal to the display unit 540. The display unit 540 may provide a user with various display contents in response to the signal (display signal) from the CPU 461.

In the example in FIG. 4, the detection circuit 315 may extract the identification code 305 detected by the sensor chip detection element 310 as an electrical signal. The CPU 461 may receive the electric signal in a digital format and specify the type of the sensor chip 300 using a value thereof. Then, the CPU 461 may recognize that it is ready to detect the Raman scattering light.

In a case where the display unit 540 indicates that it is ready to detect the Raman scattering light, a user manipulates the manipulation unit 550 to initiate the detection of the Raman scattering light. In a case where the signal from the manipulation unit 550 (manipulation signal) initiates detection, the CPU 461 may actuate the light source A through a light source driver 15. Specifically, the light source driver 15 (in the broadest sense, the CPU 461) may power on the light source A. In addition, the light source A may include a temperature sensor (not shown) and a light amount sensor (not shown). The light source A may send the temperature and the light amount of the light source A to the CPU 461 through the light source driver 15. The CPU 461 may receive the temperature and the light amount of the light source A and determine whether or not the output of the light source A is stable. While the light source A is powered on, and after the output of the light source A becomes stable in some cases, the CPU 461 may actuate the fan 450 through the fan driver 455.

In addition, the CPU 461 (in the broadest sense, the processing unit 460) may carry out the function of the control unit 7 shown in FIG. 1B, and may variably control the position of the light source A through the light source driver 15. Alternatively, the CPU 461 may variably control the position of the object lens 3 shown in FIG. 1D through the light source driver 15 or the lens driver (not shown).

In the example in FIG. 4, the fan driver 455 may power on the fan 450. As a result, the target substance (gaseous sample) is suctioned into the guide unit 420 in FIGS. 3A to 3D. In a case where the light source A in FIG. 3A is powered on, the light from the light source A reaches the sensor chip 300 in FIGS. 3A to 3D through the half mirror 2. In response, the Rayleigh scattering light and the Raman scattering light are returned to the half mirror 2 from the sensor chip 300. The Rayleigh scattering light and the Raman scattering light from the sensor chip 300 arrive at the optical filter 365 through the condensing lens 360. The optical filter 365 blocks the Rayleigh scattering light and guides the Raman scattering light to the spectroscopic element 370. The aforementioned process can be made using a fan 450 when the fluid path resistance from the inlet duct 400 (a loading entrance) to the guide unit 420 and the outlet duct 410 is relatively small. However, when the fluid path resistance is relatively large, a suction pump (not shown) may be used instead of the fan 450.

In the example in FIG. 4, the spectroscopic driver 375 (in the broadest sense, the CPU 461) may control the spectroscopic element 370. The spectroscopic element 370 may be made of a variable etalon spectroscope capable of changing the resonance wavelength. In a case where the spectroscopic element 370 is an etalon using Fabry-Perot resonance, the spectroscopic driver 375 may change (select) the wavelength of the light passing through the etalon while the distance between the two facing etalon plates is adjusted. Specifically, when the wavelength of the light passing through the etalon is set to a range from the first wavelength to the Nth wavelength, first, the distance between the two etalon plates is set such that the light of the first wavelength represents a maximum intensity. Then, the distance between the two etalon plates is set again such that the light having a second wavelength deviated by a half maximum full width from the first wavelength has a maximum intensity. In such a method, the light passing through the etalon is received by the optical receiver element 380 while the first wavelength, the second wavelength, the third wavelength, . . . , and the Nth wavelength are sequentially selected.

In the example in FIG. 4, the optical receiver circuit 385 (in the broadest sense, the CPU 461) may extract the light received from the optical receiver element 380 as an electric signal. The CPU 461 receives the electric signal in a digital format and stores the value thereof in the RAM 462. Since the spectroscopic element 370 selectively guides the light in a range of the first wavelength to the Nth wavelength to the optical receiver element 380, the CPU 461 can store the Raman spectrum in the RAM 462 in a digital format.

In the example in FIG. 4, the CPU 461 may compare the Raman spectral data unique to the target substance stored in the RAM 462 with the existing Raman spectral data stored in advance in the ROM 463. The CPU 461 may determine what kind of material the target substance is based on the comparison result. The CPU 461 may send a signal indicating the comparison result or the determination result to the display unit 540. As a result, the display unit 540 may notify a user of the comparison result or the determination result. In addition, the CPU 461 may output the data indicating the comparison result or the determination result from the communication connection plug 510. The interface 530 may transmit/receive data to/from an external device (not show) connected to the CPU 461 and the communication connection plug 510 according to a predetermined standard.

In the example in FIG. 4, the CPU 461 may determine the state of the power supply unit 470. In a case where the power supply unit 470 includes the primary battery or the secondary battery, the CPU 461 may determine whether or not the data indicating a voltage of the primary battery or the secondary battery are equal to or smaller than a predetermined value previously stored in the ROM 463. The CPU 461 may transmit the signal indicating the determination result to the display unit 540. As a result, the display unit 540 may allow a user to see the determination result (for example, out of battery, charging required) or an instruction based on the determination result. In addition, in a case where the power supply unit 470 includes the secondary battery, the CPU 461 may determine whether or not the secondary battery is being charged.

In the example in FIG. 4, the power supply unit 470 may transmit the state of the power supply unit 470 to the CPU 461. In addition, the power supply unit 470 may supply power to the processing unit 460 including the CPU 461. Although not shown in FIG. 4, the power supply unit 470 may supply power to the components of the detection apparatus such as the light source driver 15, the optical receiver circuit 385, and the light source group 1.

2.2. Light Source

Figure 5A:
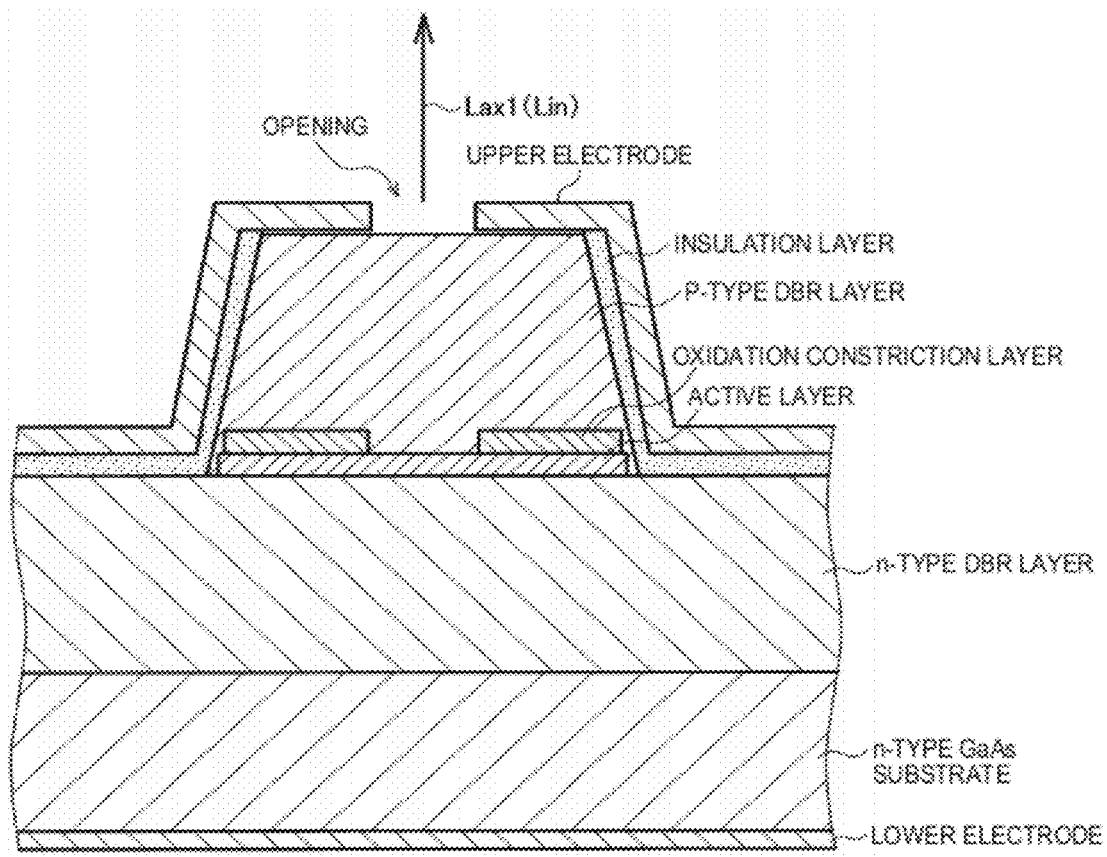
FIGS. 5A and 5B illustrate an exemplary structure of a vertical cavity surface-emitting laser (VCSEL).
Figure 5B:
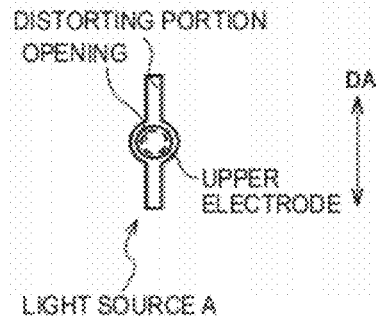

FIGS. 5A and 5B illustrate a configuration example of a VCSEL. In the example in FIG. 5A, an n-type DBR (Diffracted Bragg Reflector) layer is formed on an n-type GaAs substrate. An active layer and an oxidation constriction layer are provided at the center of the n-type diffracted Bragg reflector (DBR) layer. A p-type DBR layer is provided on the active layer and the oxidation constriction layer. An electrode is formed on the insulation layer by providing an insulation layer on the p-type DBR layer and the n-type DBR layer. The electrode is also formed on the rear side of the n-type GaAs substrate. In the example in FIG. 5A, an active layer is interposed between the n-type DBR layer and the p-type DBR layer, so that a vertical resonator is formed, in which the light generated from the active layer is resonated between the n-type DBR layer and the p-type DBR layer. In addition, the VCSEL is not limited to the example in FIG. 5A. For example, the oxidation constriction layer may be omitted.

For example, the light source A shown in FIG. 1A is preferably a VCSEL (in the broadest sense, surface-emitting laser) capable of emitting light to a direction perpendicular to the substrate surface (the optical axis Lax1 of the light source) by resonating the light in a direction perpendicular to the substrate surface. By using the VCSEL, it is possible to configure a light source which is monochromic (single wavelength) and plane-polarized. In addition, the VCSEL can be miniaturized and suitable for incorporating into a portable detection apparatus. In addition, from the structure of the VCSEL, it is possible to form a resonator without cleaving the substrate during the manufacturing process and inspect the characteristics of laser, which is suitable for mass production. Furthermore, the VCSEL can be manufactured with lower cost than those of other semiconductor laser devices, and 2-dimensional array type VCSEL can be provided as well. Furthermore, since the threshold current of the VCSEL is small, it is possible to reduce power consumption in the detection apparatus. In addition, it is possible to modulate the VCSEL in a high speed even using a low electric current, and reduce the width of the characteristic change for the temperature change of the VCSEL. In addition, it is possible to simplify the temperature control unit of the VCSEL.

By modifying the example in FIG. 5A, the VCSEL can provide a stable polarization surface (in the broadest sense, a polarization direction). In this case, instead of the polarization control element 330 in FIG. 3A the light source A (vertical cavity surface-emitting laser) may have a distorting portion as disclosed in Japanese Patent No. 3482824. In the example disclosed in Japanese Patent No. 3482824, the distorting portion 19 is disposed in the vicinity of the resonator 10B of the VCSEL. According to Japanese Patent No. 3482824, the distorting portion 19 generates birefringence and dependence on polarization of the gain within the resonator 10A by distorting the anisotropic stress to the resonator 10B. As a result, it is possible to provide a stable polarization surface.

In the example in FIG. 5B, a plan view of the VCSEL is illustrated, in which the light source A has a distorting portion. In the example in FIG. 5B, the light source A can radiate light having a polarization direction DA.

FIG. 6 is an explanatory diagram illustrating a characteristic of light sources. In the example in FIG. 6, characteristics of lasers that can be used in the light source are represented as a table. Although a VCSEL is suitable for the light source of the detection apparatus as described above, the detection apparatus may employ other kinds of laser as illustrated in FIG. 6, or light sources other than the laser.

2.3. Guide Unit

Figure 7A:
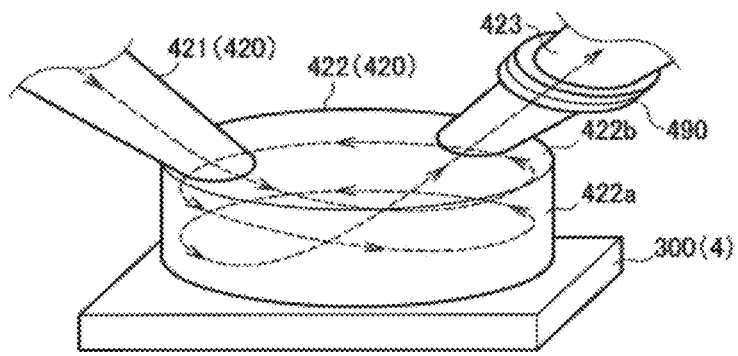
FIGS. 7A to 7C illustrate exemplary configurations of a guide unit and a discharge fluid path.
Figure 7B:
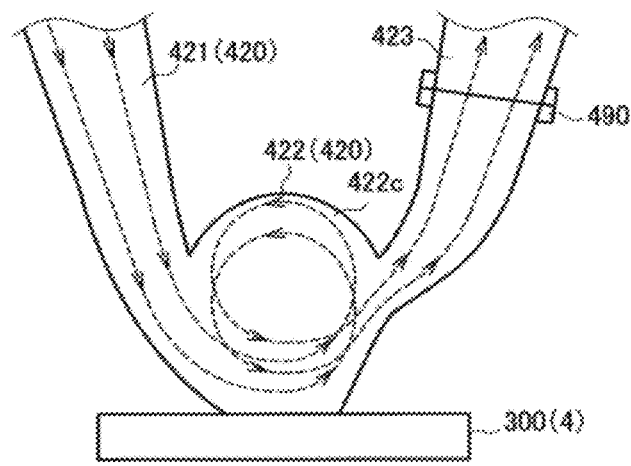
Figure 7C:
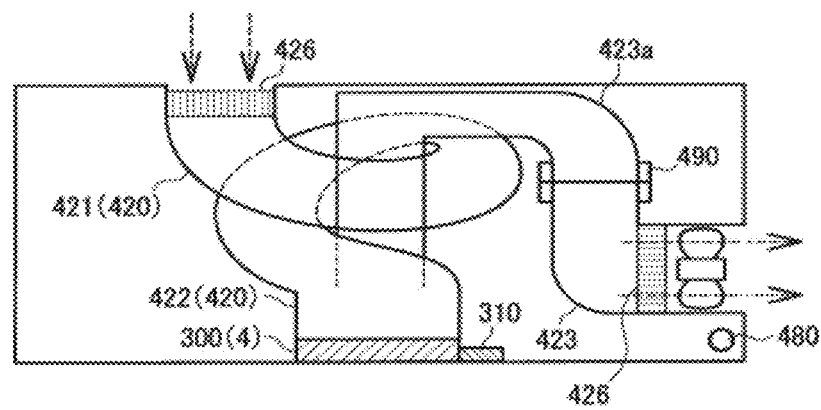

FIGS. 7A to 7C illustrate an exemplary configuration of the guide unit and the discharge fluid path 423. As shown in FIG. 7A, the fluid path 422 in the vicinity of the sensor chip 300 may have a cylindrical structure. The cylindrical structure includes an inner peripheral surface 422a and a plane 422b perpendicular to the inner peripheral surface 422a so that the gaseous sample can be rotated in a direction (horizontal direction) parallel to the plane (in the broadest sense, virtual plane) of substrate 100 (in narrow meaning, the electrical conductor) on the inner peripheral surface 422a (wall surface). Rotation of the gaseous sample in a direction parallel to the virtual plane (for example, horizontal cross-sectional surface) of the electrical conductor may be called horizontal rotation or transversal rotation. The inlet of the fluid path 422 in the vicinity of the sensor chip 300 is connected to the outlet of the inlet fluid path 421, and the outlet of the fluid path 422 in the vicinity of the sensor chip 300 is connected to the inlet of the discharge fluid path 423. The inflow direction of the gaseous sample to the inlet of the fluid path 422 from the outlet of the inlet fluid path 421 is approximated to a direction parallel to the plane 422b, so that the gaseous sample is apt to rotate in a horizontal direction. In addition, as shown in FIG. 7A, a rotating flow in a horizontal direction may be mainly generated, and a rotating flow in a vertical direction may be generated. The gaseous sample stays in the vicinity of the sensor chip 300, and then, is discharged from the discharge fluid path 423. Since the gaseous sample passes through the vicinity of the enhanced electric field near the sensor chip 300 several times, a possibility that the gaseous sample enters the enhanced electric field increases.

As shown in FIG. 7B, the fluid path 422 near the sensor chip 300 may have a cavity-shaped structure. The cavity-shaped structure has an inner spherical surface 422c. The gaseous sample can be rotated in a direction (vertical direction) perpendicular to the virtual plane of the electrical conductor on the inner spherical surface 422c (wall surface). Rotation of the gaseous sample in a direction perpendicular to the virtual plane (for example, a horizontal cross section) of the electrical conductor may be called vertical rotation or longitudinal rotation. Since the inflow direction of the gaseous sample from the outlet of the inlet fluid path 421 to the inlet of the fluid path 422 is approximated to a direction perpendicular to the plane 422b, the gaseous sample is apt to rotate in a vertical direction. In addition, as shown in FIG. 7B, the rotation flow in a vertical direction is mainly generated, and the rotation flow in a horizontal direction may be generated.

In the example in FIG. 7C, the inlet fluid path 421 may have a helical structure. The gaseous sample enters the fluid path 422 from the inlet fluid path 421. In this case, since the inlet fluid path 421 has a helical structure, a rotating gaseous sample enters the fluid path 422. Therefore, since the gaseous sample may further rotate in the fluid path 422, a possibility that the gaseous sample stays in the enhanced electric field near the electric conductor further increases. In addition, the inlet fluid path 421 can block the external light, and the inner wall of the inlet fluid path 421 is preferably made of a material having low light reflectivity to increase the light blocking property. In the example in FIG. 7C, the guide unit 420 (in the broadest sense, optical device unit) may have a relay path 423a connectable to the discharge fluid path 423.

The discharge fluid path 423 may have a helical structure as shown in FIG. 7C. In addition the inlet fluid path 421 shown in FIG. 7A may have a helical structure.

2.4. Optical Device (Metal Nano-Structure According to a Photolithographic Technique)

FIGS. 8A to 8E are schematic explanatory diagrams illustrating a photolithographic technique. In the example in FIG. 8A, an optical interferotype exposure apparatus using ultraviolet laser is schematically illustrated, and continuous wave (CW) laser having a wavelength of 266 nm and an output power of 200 mW may be used as the light source. The light from the ultraviolet laser is reflected at the mirror via a shutter and splits into both sides of the half mirror. The two light beams split from the half mirror are reflected at the mirror and pass through the object lens and the pinhole so that the diameters of the light beams are enlarged. An exposure pattern may be formed by irradiating the light from the ultraviolet laser having an enlarged beam diameter onto a mask, and the exposure pattern may be irradiated onto the substrate 100 where a photoresist has been coated. In this case, since the exposure patterns from both masks are interfered with each other, an interference pattern can be formed on the photoresist (substrate 100). In addition, it is possible to recognize the exposure pattern on a monitor using a half mirror or a CCD camera.

After a predetermined interference pattern (in the broadest sense, a predetermined exposure pattern) is exposed on the photoresist (substrate 100), it is possible to leave only a desired part of the photoresist by developing the photoresist. Then, the substrate 100 may be etched to as much as the necessary amount by immersing it into an etching solution or through dry etching. After the etching, the photoresist remaining on the substrate 100 may be removed. As a result, it is possible to manufacture the surface of the substrate 100 in a fine embossed shape. Then, it is possible to form a metal nano-structure by adding metal fine-particles as an electrical conductor on the surface of the substrate 100. An overview of the manufacturing process of the metal nano-structure will be described below (refer to FIGS. 9A to 9E).

Figure 8A:
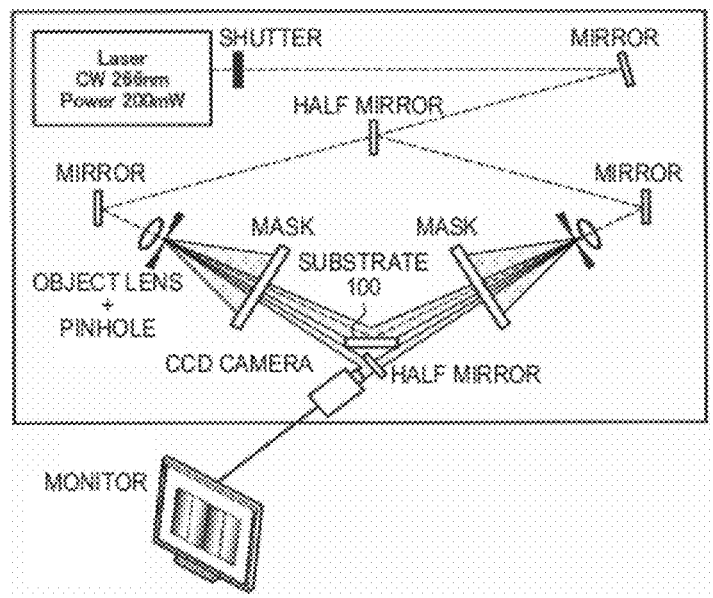
FIGS. 8A to 8E are schematic explanatory diagrams illustrating a photolithographic technique.
Figures 8B, 8C:
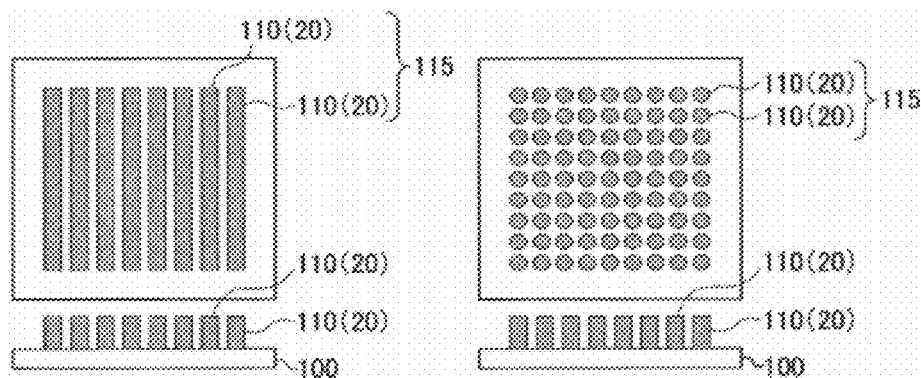

In the example in FIG. 8B, a substrate 100 having a metal nano-structure is illustrated in a plan view and a cross-sectional view. In this example, the substrate 100 (metal nano-structure) includes a protrusion group 115 including a plurality of protrusions 110, and a plurality of protrusions 110 (metal fine-particles 20) are periodically arranged in a one-dimensional space.

Also in the example in FIG. 8C, the substrate 100 having a metal nano-structure is illustrated in a plan view and a cross-sectional view. In this example, a plurality of protrusions 110 (metal fine-particles 20) are periodically arranged in a two-dimensional space. In the example in FIG. 8D, the substrate 100 having a metal nano-structure is illustrated as an electron microscope photograph in a perspective view and corresponds to FIG. 8C. In the example in FIG. 8D, the substrate 100 having a metal nano-structure is illustrated in a plan view as a scanning electro microscopy (SEM) photograph, and corresponds to FIG. 8C. For example, a period (pitch) of a plurality of protrusions 110 containing gold (Au) is set to approximately 140 nm.

In addition, the metal nano-structure may be formed using an electron beam exposure apparatus instead of the optical interferotype exposure apparatus. While the electron beam exposure apparatus is advantageous in view of a higher exposure freedom in comparison with the optical interferotype exposure apparatus, the optical interferotype exposure apparatus is advantageous in view of higher productivity of the optical device in comparison with the electron beam exposure apparatus.

FIGS. 9A to 9E are schematic explanatory diagrams illustrating a manufacturing process of the metal nano-structure.

Figure 9A:
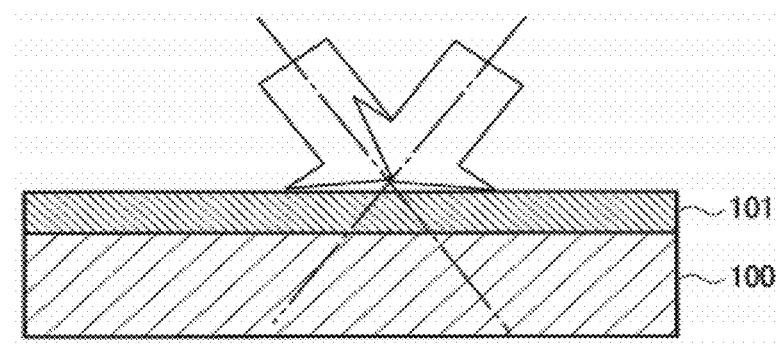
FIGS. 9A to 9E are schematic explanatory diagrams illustrating a manufacturing process of a metal nano-structure.

In the following description, like reference numerals denote like elements as in FIG. 8B, and description thereof will not be repeated. For example, the metal nano-structure illustrated in FIG. 8C may be manufactured, specifically, as described below. As shown in FIG. 9A, the substrate 100 has a photoresist 101. The photoresist 101 is coated on the substrate 100 using a spin coat, and then, dried. In order to expose the predetermined pattern on the photoresist 101 an optical interferotype exposure apparatus as shown in FIG. 8A may be used. For example, a positive photoresist may be used as the photoresist 101, and the thickness of the photoresist 101 may be set to 1 μm. In the example in FIG. 9A, the light beams from two directions are irradiated onto the photoresist 101, and each of the two light beams has an exposure pattern having a lattice shape. It is possible to form various interference patterns using a crossing angle between the two light beams. In addition, the size of the interference pattern may be reduced to a half of the wavelength of the ultraviolet laser in the optical interferotype exposure apparatus. A latent image generated by the interference pattern is formed in the photoresist 101, and the photoresist 101 is developed. As a result, it is possible to form a photoresist pattern as shown in FIG. 9B.

Figure 9B:
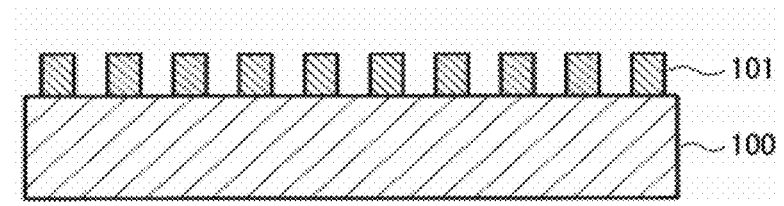
Figure 9C:
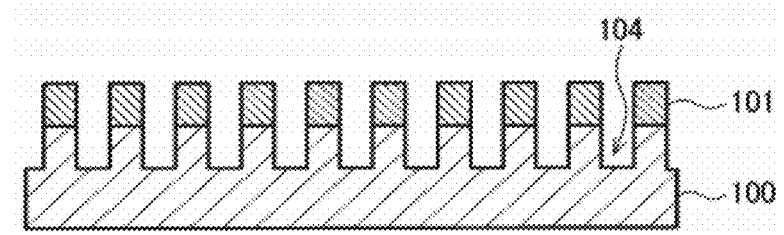
Figure 9D:
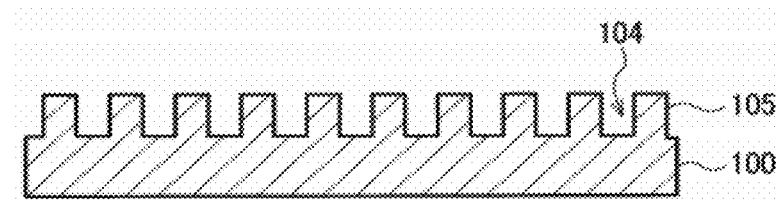
Figure 9E:
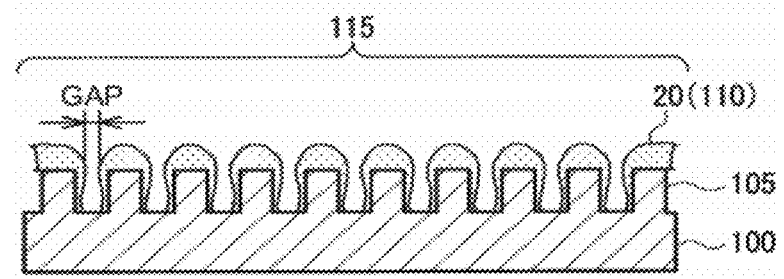

As shown in FIG. 9B, the substrate 100 includes a portion protected by the photoresist pattern and a portion unprotected by the photoresist pattern. Then, the portion unprotected by the photoresist pattern is etched to form a concave portion 104 in the substrate 100 as shown in FIG. 9C. Then, by removing the photoresist 101 remaining in the substrate 100 the convex portion 105 of the substrate 100 shown in FIG. 9D is exposed. Then a metal film containing metal fine-particles 20 is formed on the substrate 100 using a sputtering apparatus. Although a thin metal film is formed on the entire area of the substrate 100 in an initial state, a lot of metal fine-particles 20 are gradually adhered in the vicinity of the convex portion 105 so that a plurality of protrusions 110 (metal nano-structure) can be formed in the metal film as shown in FIG. 9E.

If plane-polarized laser light is irradiated onto the protrusion group 115 including a plurality of protrusions 110 (the metal nano-structure), localized plasmons are excited by the polarization direction of the laser light, and a strong enhanced electric field is formed in the gap between the neighboring protrusions 110 in the protrusion group 115. The gap between the neighboring protrusions 110 in the protrusion group 115 can be controlled using the thickness of the metal film. The size of the gap serves as a main factor for controlling the strength of the enhanced electric field.

The metal fine-particle 20 or the metal film may be formed of aurum (gold) (Au), silver (Ag), copper (Cu), aluminum (Al), palladium (Pd), platinum (Pt), or alloy thereof (a combination thereof). Preferably, the metal fine-particles 20 or the metal film may be formed of gold (Au) or silver (Ag) to make it easier to generate the localized plasmon, the enhanced electric field, or the surface-enhanced Raman scattering.

Figure 10A:
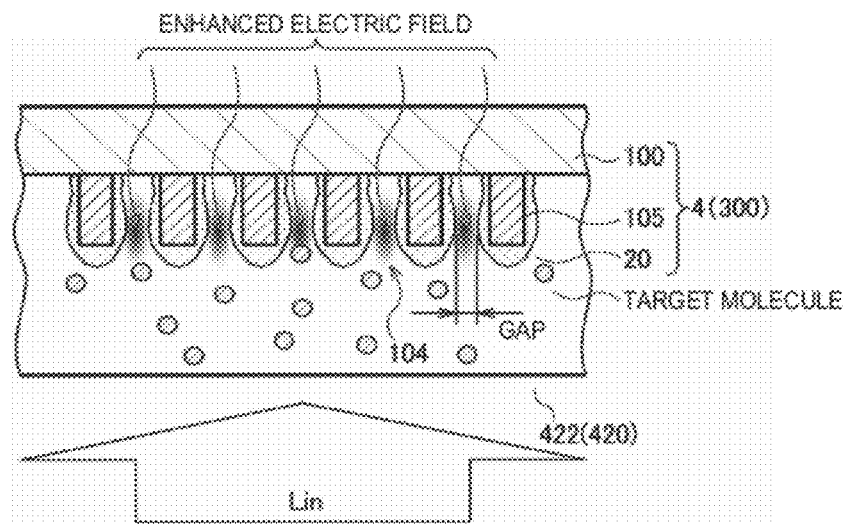
FIGS. 10A to 10C are schematic explanatory diagrams illustrating an enhanced electric field formed in a metal nano-structure.
Figure 10B:
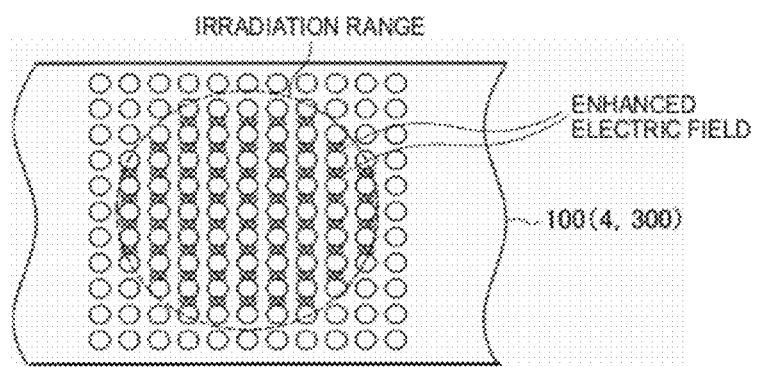
Figure 10C:
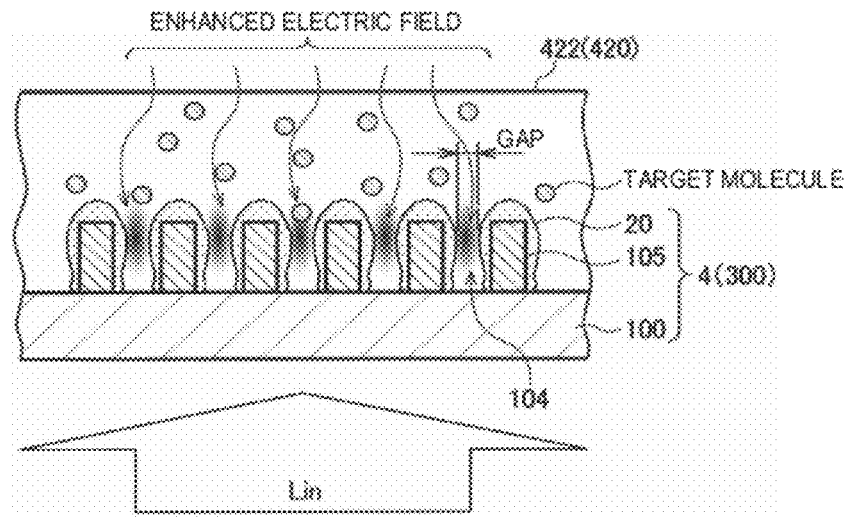

FIGS. 10A to 10C are schematic explanatory diagrams illustrating the enhanced electric field formed from the metal nano-structure. In the following description, like reference numerals denote like elements as in FIG. 2D, and description thereof will not be repeated. The target molecule (gaseous sample) is suctioned to the inner side of the guide unit 420 from the inlet duct 400 as shown in FIG. 3A and reaches the fluid path 422 in the vicinity of the sensor chip 300 (in the broadest sense, the optical device 4). In the example in FIG. 10A, the optical device 4 includes a metal nano-structure. If the light Lin (incident light) is irradiated from the light source to the metal nano-structure, the enhanced electric field is formed in the gap of the convex portion 105. In the example in FIG. 10B, an irradiation range of the light Lin (incident light) is illustrated as a dotted line. In addition, in a case where the target molecule enters the enhanced electric field, the Raman scattering light is generated including information on the frequency of the target molecule. In addition, the Raman scattering light is enhanced by the enhanced electric field, and the surface-enhanced Raman scattering is generated. Although the incident light is irradiated from the rear side (the substrate 100 side) of the optical device 4 in the example in FIG. 10A, the incident light may be irradiated from the surface side of the sensor chip 300 (the convex portion 105 side), as shown in FIG. 10C.

If the gap between the convex portions 105 becomes small and the height of the convex portion 105 (the depth of the concave portion 104) becomes large, generally, the enhanced electric field shown in FIG. 10A becomes strong. In addition, as the intensity of the light Lin (incident light) becomes higher, the enhanced electric field becomes strong. However, if the gap between the convex portions 105 is too narrow, the probability in which the target molecule enters the gap (enhanced electric field) becomes low. Therefore, the gap between the convex portions 105 can be set to several nm to several tens nm, for example. Further, if the height of the convex portion 105 (the depth of the concave portion 104) becomes large, the time in which the target molecule exits from the gap (enhanced electric field) after entering the gap (enhanced electric field) can be increased, and the detection signal or the Raman spectrum representing the Raman scattering light becomes stable.

In addition, the wavelength of the light Lin (incident light) may be selected based on the type of the metal of the metal nano-structure. In a case where the metal nano-structure is formed of gold (Au), the wavelength of the light Lin may be set to 633 nm. In addition, in a case where the metal nano-structure is formed of silver (Ag), the wavelength of the light Lin may be set to 514 nm. In addition, it is possible to select the wavelength of the light Lin depending on the type of the target molecule. In addition, in a case where the gaseous sample contains impurities other than the target molecule, the wavelength of the light Lin may be set to 780 nm in order to suppress fluorescence of the impurities.

2.5. Surface Plasmon Resonance Peak

When the light Lin (incident light) is irradiated onto the metal nano-structure (in the broadest sense, an electrical conductor) of the optical device 4 illustrated in FIG. 10C, typically, only a single broad surface plasmon resonance peak exists. Therefore, it is necessary to set the position of the resonance peak to a suitable position in consideration of the excitation wavelength (equal to the Rayleigh scattering wavelength) and the Raman scattering wavelength. Therefore, if the resonance peak wavelength is set to a value between the excitation wavelength and the Raman scattering wavelength, it is possible to anticipate the electric field enhancement effect in both the excitation process and the Raman scattering process. However, since the resonance peak is broad, the intensity of the resonance is reduced in individual processes, and it can be said that the enhancement degree of the entire process is not sufficient. In this regard, it is possible to improve the detection sensitivity and the sensor sensitivity by introducing the incident light to the optical device 4 with an inclination to generate two resonance peaks and setting the two resonance peaks as the excitation wavelength and the Raman scattering wavelength.

In order to implement a high-sensitivity sensor chip 300 (in the broadest sense, the optical device 4) by applying the surface-enhanced Raman scattering, it is preferable that the enhancement degree of the local electric field (hereinafter, simply referred to as an enhancement degree) increases as large as possible. The enhancement degree $\alpha$ can be expressed as the following Equation (1) (M. Inoue, K. Ohtaka, J. Phys. Soc. Jpn., 52, 3853 (1983). In the Equation (1), $\alpha$ray denotes an enhancement degree using the excitation wavelength, and $\alpha$ram denotes the enhancement degree using the Raman scattering wavelength.

$$\alpha = \alpha\text{ray} \times \alpha\text{ram} \quad (1)$$

Figure 11:
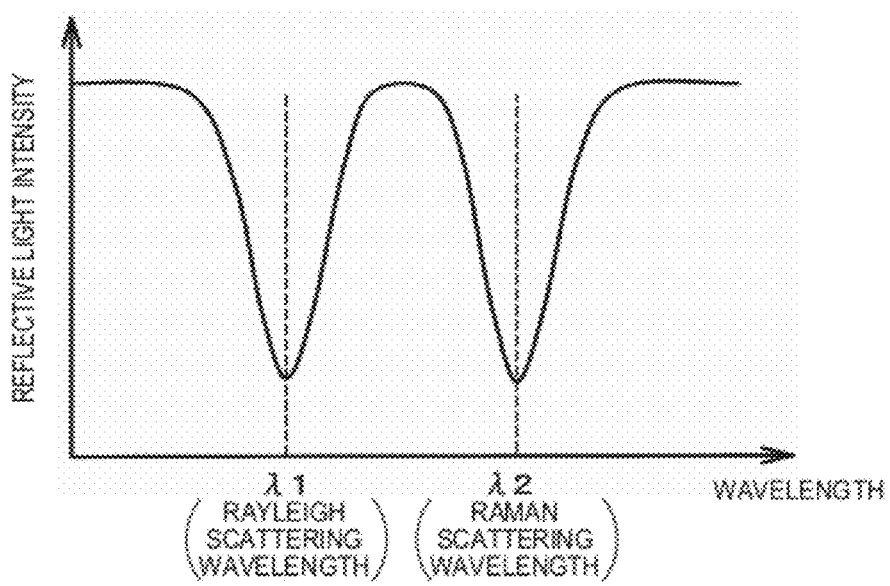
FIG. 11 is a schematic explanatory diagram illustrating two resonance peaks.

Based on the Equation (1) described above, it is possible to increase the enhancement degree in the course of the surface-enhanced Raman scattering by simultaneously increasing both the enhancement degree in the excitation process and the enhancement degree in the Raman scattering process. Therefore as shown in FIG. 11, it is possible to generate two resonance peaks that are strong only in the vicinity of the excitation wavelength and the Raman scattering wavelength. As a result, it is possible to increase the enhancement effect of the local electric field by a synergy effect of both scattering processes.

Figure 12:
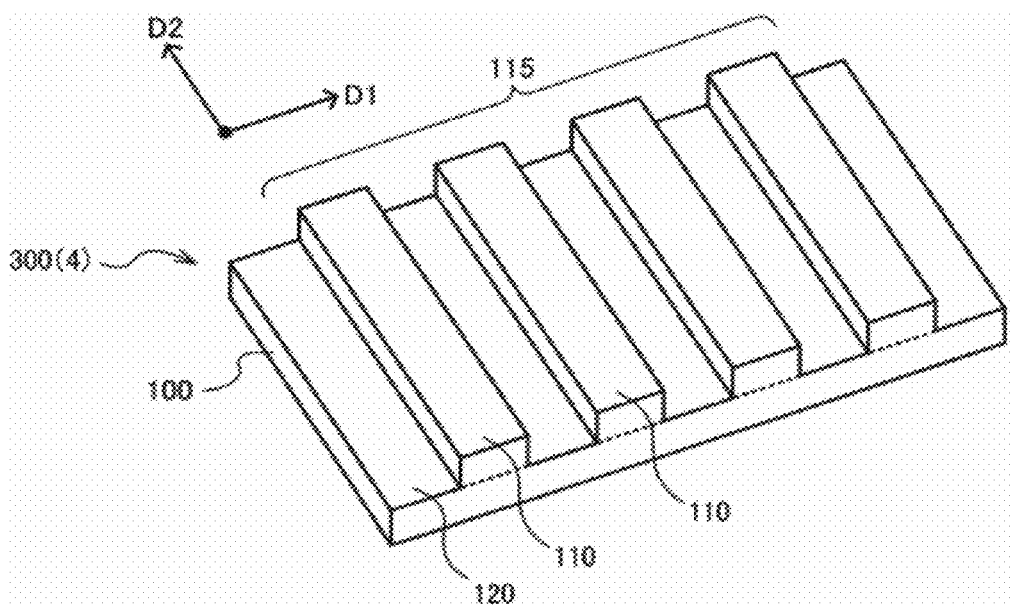
FIG. 12 is a perspective view illustrating a configuration example of a sensor chip.

FIG. 12 is a perspective view illustrating a configuration example of the sensor chip. As shown in FIG. 12, the sensor chip 300 includes a substrate 100 (base material) and a protrusion group 115 (a first protrusion group). The protrusion group 115 having a plurality of protrusions 110 contains an electrical conductor, and the electrical conductor is typically formed of metal (for example, gold (Au)) or may be formed of a semiconductor (for example, poly-silicon).

Figures 8D, 8E:
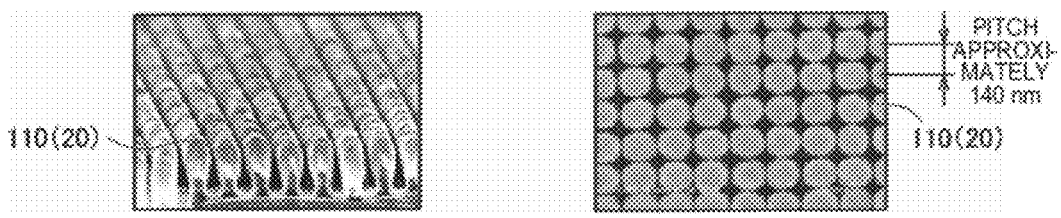

A plurality of protrusions 110 are periodically arranged in the first direction D1 along the plane of the substrate 100 (in the broadest sense, a virtual plane). Here, the plane of the substrate 100 is the surface 120 of the substrate 100 where the protrusion group 115 is formed, and may be a plane parallel to the surface 120. More specifically, each protrusion 110 of the protrusion group 115 is formed to have a convex shape from the surface 120 of the substrate 100 in a cross-sectional shape of the arrangement direction of the protrusions (first direction D1). The convex shape may include a rectangular shape, a trapezoidal shape, a circular arc shape. For example, a cross-sectional shape defined by complicated curves as shown in FIGS. 8D and 9E may be used. For example, as shown in FIG. 12, the protrusion group 115 is formed to have a parallel stripe shape in the second direction D2 perpendicular to the first direction D1 as seen in a plan view for the substrate 100.

Figure 13:
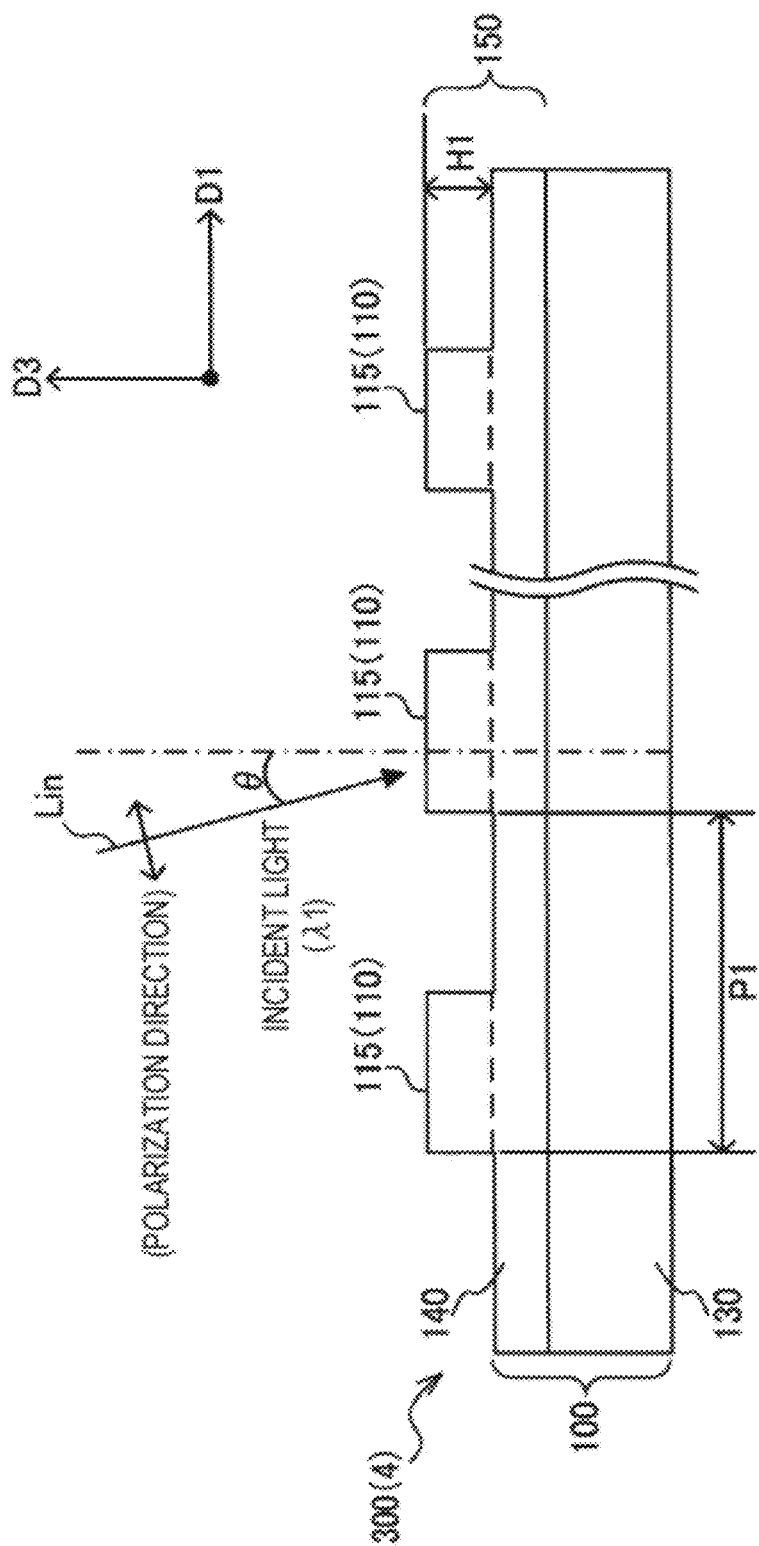
FIG. 13 is a cross-sectional view illustrating the sensor chip of FIG. 12.

FIG. 13 is a cross-sectional view illustrating a sensor chip in FIG. 12. The cross section of this cross-sectional view is perpendicular to the plane of the substrate 100 and parallel to the arrangement direction of the protrusion group 115 (first direction D1). As shown in FIG. 13, the direction normal to the plane of the substrate 100 is set to a third direction D3.

In the example in FIG. 13, the substrate 100 has a glass substrate 130 and a metal thin film 140 formed on the glass substrate 130. For example, the metal thin film 140 has a thickness equal to or larger than 150 nm. In the example in FIG. 13, the cross-sectional shape of the protrusion group 115 is rectangular (approximately rectangular), and the protrusions 110 having a first height H1 are arranged with a first period P1 along the first direction D1. A metal lattice 150 (periodically embossed metal structure) is formed by the metal thin film 140 and the protrusion group 115. The first period P1 is preferably set to a range between 100 and 1000 nm, and the first height H1 is preferably set to a range between 10 and 100 nm. In addition, the glass substrate 130 may be substituted with a quartz substrate, a sapphire substrate. The substrate 100 may be formed using a metal plate.

The incident light Lin including plane polarization may be incident to the sensor chip 300. The direction (polarization orientation) of the plane polarization is parallel to the surface parallel to the first direction D1 and the third direction D3. In the example in FIG. 13, the incident light Lin is incident with an inclination with respect to the metal lattice 150 including the metal thin film 140 and the protrusion group 115 (in the broadest sense, an electrical conductor). Specifically, if the inclination angle is set to θ, θ>0. The incident light is incident such that an angle between the direction incident to the cross section in FIG. 13 and the direction opposite to the third direction D3 (an angle with respect to the normal line directed to the plane of the substrate 100) becomes θ.

Preferably, the plane polarization is parallel to the surface parallel to the first direction D1 and the third direction D3. However, the plane polarization may be nonparallel to the plane parallel to the first direction D1 and the third direction D3. In other words, the plane polarization may contain a polarization component parallel to the surface parallel to the first direction D1 and the third direction D3. In addition, the polarization direction of the plane polarization may be set by the distorting portion in FIG. 5B, the polarization control element 330 in FIG. 3A.

Figure 14:
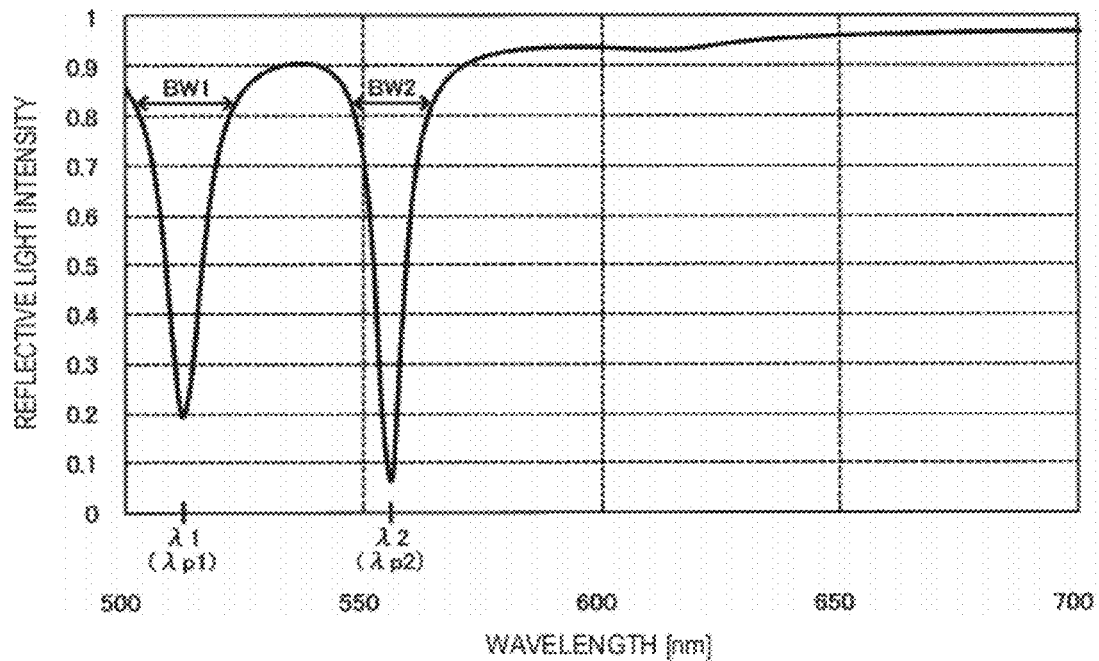
FIG. 14 illustrates an exemplary characteristic of a reflective light intensity of a sensor chip.

FIG. 14 illustrates an exemplary characteristic of the reflective light intensity of the sensor chip. FIG. 14 illustrates an exemplary characteristic in the event that the metal lattice 150 is formed of silver Ag, the incident angle θ of the light for the metal lattice 150 is set to 3°, the polarization direction of the light is perpendicular to the groove direction of the metal lattice 150 (second direction D2), the cross section of the protrusion 110 has a rectangular shape (approximately rectangular), the first period P1 is set to 500 nm, and the first height H1 is set to 20 nm. In the example in FIG. 14, the abscissa denotes the wavelength of the reflective light, and the ordinate denotes the reflective light intensity (a ratio with respect to the incident light intensity).

In the example in FIG. 14, two resonance peaks of the surface plasmon polaritons (SPP) exist in the metal lattice 150. For example, a single resonance peak wavelength λp1 is positioned in the vicinity of 515 nm, and the other resonance peak wavelength λp2 is positioned in the vicinity of 555 nm. It is possible to obtain a significant enhanced Raman scattering effect by matching or adjusting the two resonance peak wavelengths λp1 and λp2 to the vicinity of the excitation wavelength λ1 and the Raman scattering wavelength λ2, respectively. For example, in a case where Argon laser having a wavelength of 515 nm is used as the excitation wavelength λ1, it is possible to strongly enhance the Raman scattering light in the vicinity of a wavelength of 555 nm (Raman shift of 1200 to 1600 $cm^{-1}$).

Figure 15:
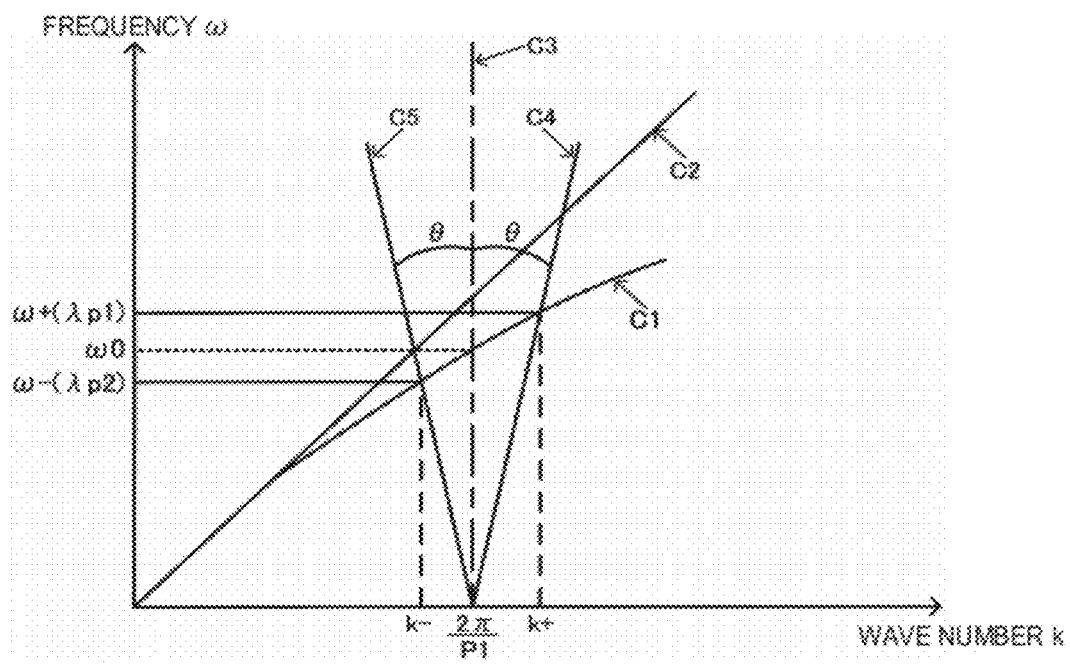
FIG. 15 is an explanatory diagram illustrating an excitation condition of surface plasmon polaritons.

FIG. 15 is an explanatory diagram illustrating an excitation condition of the surface plasmon polaritons. The reference numeral C1 in FIG. 15 denotes a distribution curve of the surface plasmon polaritons (for example, a distribution curve at the interface between the air and gold (Au)), and the reference numeral C2 denotes a light line. In FIG. 15, the period of the metal lattice 150 is set to a first period P1, and the wave number $2\pi/P1$ of the lattice vector in this case is illustrated on the abscissa.

First, a relationship between the metal lattice 150 and the excitation condition will be described. If the wave number of the incident light Lin is denoted by ki, and the incident angle is denoted by θ, the wave number of the primary evanescent wave in the arrangement direction of the metal lattice 150 (the first direction D1 in FIG. 13 or the opposite direction of the first direction D1) is set to $2\pi/P1 \pm ki \cdot \sin\theta$. The surface plasmon polaritons are excited when the wave number $2\pi/P1 \pm ki \cdot \sin\theta$ of the evanescent wave and the wave number of the surface plasmon match each other. That is, the excitation condition of the surface plasmon polaritons is deter-mined by the cross point between the straight line indicating a condition for generating the evanescent wave and a distribution curve of the surface plasmon polaritons.

In C3 in FIG. 15, as a comparison example, a straight line indicating a condition for generating the evanescent wave when light is incident perpendicularly (θ=0) to the metal lattice 150 is illustrated. As shown in C3, the wave number of the evanescent wave in this case is represented as $2\pi/P1$. The straight line C3 is a line extending on the position of the wave number of the lattice vector, and intersects with the distribution curve C1 of the surface plasmon polaritons. In this case, a single cross point exists, and a resonance peak corresponding to the frequency ω0 (angular frequency) is generated.

In C4 and C5, a straight line indicating a condition for generating the evanescent wave is illustrated. In a case where light is incident with an angle θ (θ>0) with respect to the metal lattice 150, the wave number of the evanescent wave can be expressed as $2\pi/P1 \pm ki \cdot \sin\theta$. The straight line C4 corresponds to $2\pi/P1 + ki \cdot \sin\theta$, and the straight line C5 corresponds to $2\pi/P1 - ki \cdot \sin\theta$. Such straight lines C4 and C5 extend from the position of the wave number of the lattice vector with an inclination angle θ, and intersect with the distribution curve C1 of the surface plasmon polaritons at two points (frequencies ω+ and ω−). Therefore, the two resonance peaks corresponding to the frequencies ω+ and ω− are represented as resonance peak wavelengths λp1 and λp2.

Two resonance peak wavelengths λp1 and λp2 are set using the excitation condition of the surface plasmon polaritons, and the two resonance peak wavelengths λp1 and λp2 can be used in the surface-enhanced Raman scattering. Specifically, first, the distribution curve C1 is obtained using a rigorous coupled wave analysis (RCWA) (L. Li and C. W. Haggans, J. Opt. Soc. Am., A10, 1184-1189 (1993)). The distribution curve C1 is unique to the type of the metal, the type of the medium, or a cross-sectional shape of the metal lattice 150. Then, a predetermined lattice period (for example, the first period P1) and a predetermined incident angle θ are determined depending on the Raman shift of the target substance. That is, the first resonance peak wavelength λp1 is set in the vicinity of the excitation wavelength λ1 (Rayleigh scattering wavelength), and the second resonance peak wavelength λp2 (λp2>λp1) is set in the vicinity of the Raman scattering wavelength λ2. In addition, the predetermined first period P1 and the predetermined incident angle θ may be set such that the straight line C4 passes through the cross point between the distribution curve C1 and ω=ω+(λ=λp1), and the straight line C5 passes through the cross point between the distribution curve C1 and ω=ω−(λ=λp2).

In the example in FIG. 14, the first resonance peak wavelength band BW1 including the first resonance peak wavelength λp1 includes the excitation wavelength λ1 in the surface-enhanced Raman scattering. The second resonance peak wavelength band BW2 including the second resonance peak wavelength λp2 includes the Raman scattering wavelength λ2 in the surface-enhanced Raman scattering. Since the first period P1 and the incident angle θ are set such that the resonance peak wavelength bands BW1 and BW2 include the resonance peak wavelengths λ1 and λ2, respectively, it is possible to improve the electric field enhancement degree in the excitation wavelength λ1 and the electric field enhancement degree in the Raman scattering wavelength λ2.

Here, the resonance peak wavelength bands BW1 and BW2 are bandwidths at the predetermined reflective light intensity, and may be a half-maximum full width of the peak. In addition, although λ1=λp1 and λ2=λp2 in FIG. 14, λ1 may be different from λp1, and λ2 may be different from λp2.

Figure 16:
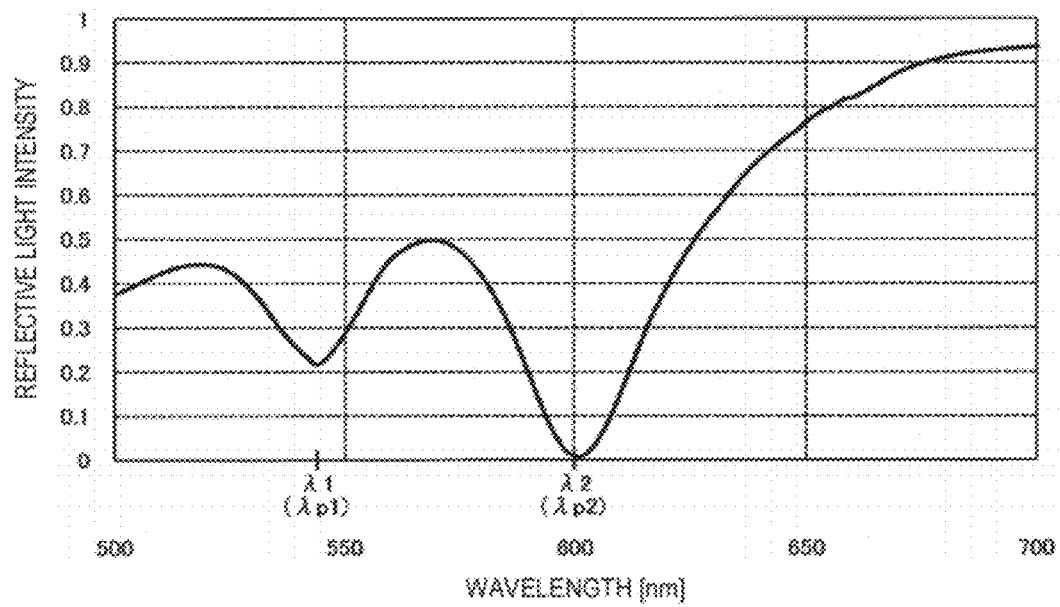
FIG. 16 illustrates another exemplary characteristic of a reflective light intensity of a sensor chip.

FIG. 16 illustrates another exemplary characteristic of the reflective light intensity of the sensor chip. FIG. 16 illustrates an exemplary characteristic in the event that the metal lattice 150 is formed of gold (Au), the incident angle θ of the light with respect to the metal lattice 150 is set to 5°, the polarization direction of the light is perpendicular to the groove direction of the metal lattice 150 (second direction D2), the cross section of the protrusion 110 is rectangular (approximately rectangular), the first period P1 is set to 500 nm, and the first height H1 is set to 40 nm.

In the example in FIG. 16, a single resonance peak wavelength λp1 is positioned in the vicinity of 545 nm, and the other resonance peak wavelength λp2 is positioned in the vicinity of 600 nm. It is possible to obtain a significant enhanced Raman scattering effect by adjusting or matching the two resonance peak wavelengths λp1 and λp2 in the vicinities of the excitation wavelength λ1 and the Raman scattering wavelength λ2, respectively.

In the example in FIG. 16, compared to the example in FIG. 14, two resonance peaks are slightly broad and shallow. However, in comparison with the case where only a single resonance peak is used, the effect of enhancing the signal of the surface-enhanced Raman scattering is excellent. In addition, it is possible to suppress surface degradation caused by oxidation and sulfurization by using gold (Au).

Figure 17:
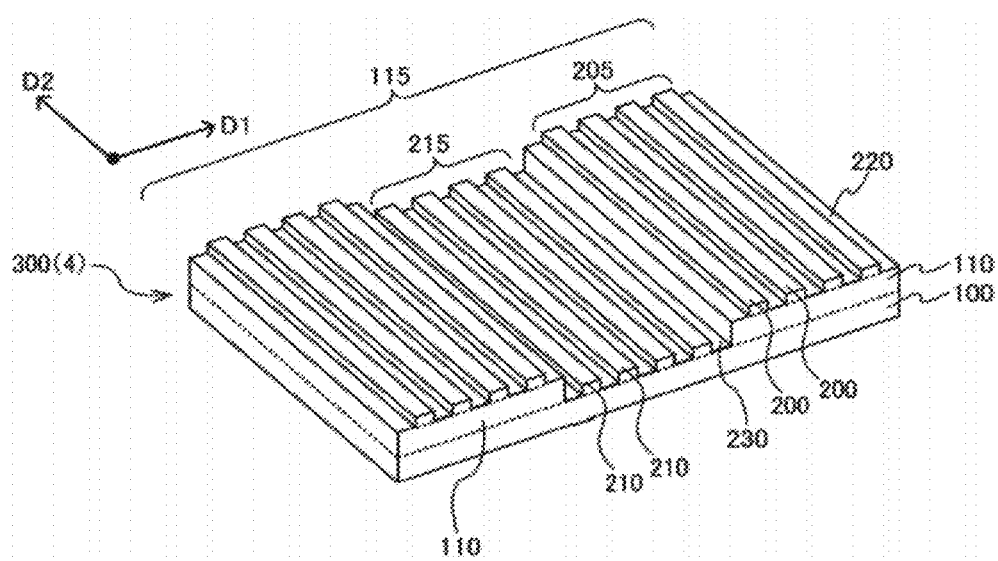
FIG. 17 is a perspective view illustrating a modified example of the sensor chip of FIG. 12.

FIG. 17 is a perspective view illustrating a modified example of the sensor chip of FIG. 12. Hereinafter, like reference numerals denote like elements as in FIG. 12, and description thereof will not be repeated. In the example in FIG. 12, the incident light Lin is preferably plane-polarized such that a component parallel to the plane of the substrate 100 of the polarization direction (the orthograph with respect to the plane of the substrate 100 of the polarization direction) is parallel to the arrangement direction of the first protrusion group 115 (first direction D1). As a result, a compression wave of the free electron plasma is generated by the plane polarization along the first direction D1, and it is possible to excite the surface plasmon propagating along the arrangement direction of the first protrusion group 115.

In the example in FIG. 17, a second protrusion group 205 formed of metal may be included on the top surface 220 of the first protrusion group 115. Each of a plurality of protrusions 200 of the second protrusion group 205 is arranged with a second period P2 (P2<P1) shorter than the first period P1 along the direction parallel to the plane of the substrate 100 (first direction D1).

In addition, in the example in FIG. 17, a third protrusion group 215 formed of metal may be included in the surface between the neighboring protrusions 110 of the first protrusion group 115 on the surface where the first protrusion group 115 is arranged (the bottom surface 230 between the neighboring protrusions 110 of the first protrusion group 115). Each of a plurality of protrusions 210 of the third protrusion group 215 is arranged with a third period P3 (P3<P1) shorter than the first period P1 along the direction parallel to the plane of the substrate 100 (first direction D1).

As a result, the propagation type surface plasmon is excited by the first protrusion group 115, and the localized surface plasmon is excited by that propagation type surface plasmon in the second protrusion group 205 or the third protrusion group 215. As a result, it is possible to further improve the electric field enhancement degree in the excitation wavelength λ1 and the Raman scattering wavelength λ2.

The protrusions 200 and 210 of the second protrusion group 205 and the third protrusion group 215, respectively, are formed such that a cross-sectional shape in the arrangement direction of the protrusions 200 and 210 (first direction D1) has a convex shape from the top surface 220 and the bottom surface 230. The convex shape includes a rectangular shape, a trapezoidal shape and a circular arc shape. For example, as shown in FIG. 17, the second protrusion group 205 or the third protrusion group 215 is formed to have a stripe shape parallel to the second direction D2 as seen in a plan view with respect to the substrate 100. The second protrusion group 205 and the third protrusion group 215 may be formed of the same metal as that of the first protrusion group 115 or may be formed of other metal materials.

Figure 18:
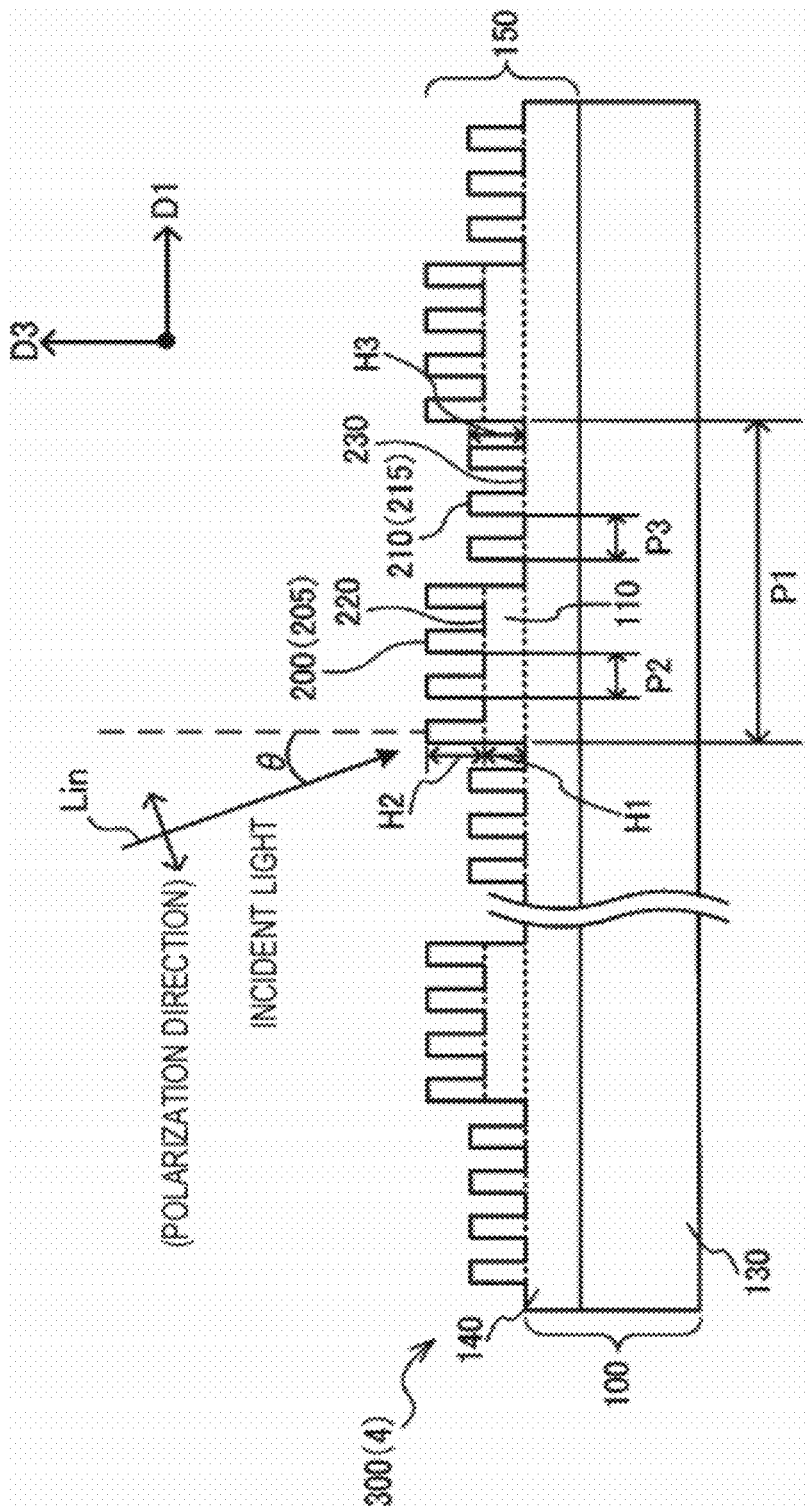
FIG. 18 is a cross-sectional view illustrating the sensor chip of FIG. 17.

FIG. 18 is a cross-sectional view illustrating the sensor chip of FIG. 17. The cross section of FIG. 18 is perpendicular to the plane of the substrate 100 and parallel to the first direction D1. As shown in FIG. 18, the protrusions 200 having a second height H2 from the top surface 220 (the second protrusion group 205) are arranged with a second period P2 shorter than the first period P1. The protrusions 210 (the third protrusion group 215) having a third height H3 from the bottom surface 230 are arranged with a third period P3 shorter than the first period P1. For example, the second period P2 or the third period P3 is preferably set to be equal to or shorter than 500 nm, and the second height H2 or the third height H3 is preferably set to be equal to or shorter than 200 nm. In addition, the third height H3 may be set to be H3>H1 or H3≦H1.

In the example in FIG. 18, the arrangement direction of the second protrusion group 205 or the third protrusion group 215 is the same as the arrangement direction of the first protrusion group 115 (the first direction D1). However, the arrangement direction of the second protrusion group 205 or the third protrusion group 215 may be different from the first direction D1. In this case, the second period P2 or the third period P3 becomes the arrangement period in the first direction D1.

As described above, using the first protrusion group 115, propagation type surface plasmons having two resonance peaks in the excitation wavelength λ1 (Rayleigh scattering wavelength) and the Raman scattering wavelength λ2 are excited. The surface plasmons propagate along the surface of the metal lattice 150 and excite the localized surface plasmons in the second protrusion group 205 or the third protrusion group 215. In addition, the localized surface plasmons excite the enhanced electric field between the protrusions 200 and 210 of the second protrusion group 205 or the third protrusion group 215, and the surface-enhanced Raman scattering is generated by the interaction between the enhanced electric field and the target substance. In this case, since the interval between the protrusions 200 and 210 of the second protrusion group 205 or the third protrusion group 215 is narrow, a strong enhanced electric field is excited between the protrusions 200 and 210. For this reason, regardless of whether the number of target substances adsorbed between the protrusions 200 and 210 is singular or plural, it is possible to generate the surface-enhanced Raman scattering by the enhanced electric field.

2.6. Incident Angle

Figure 19A:
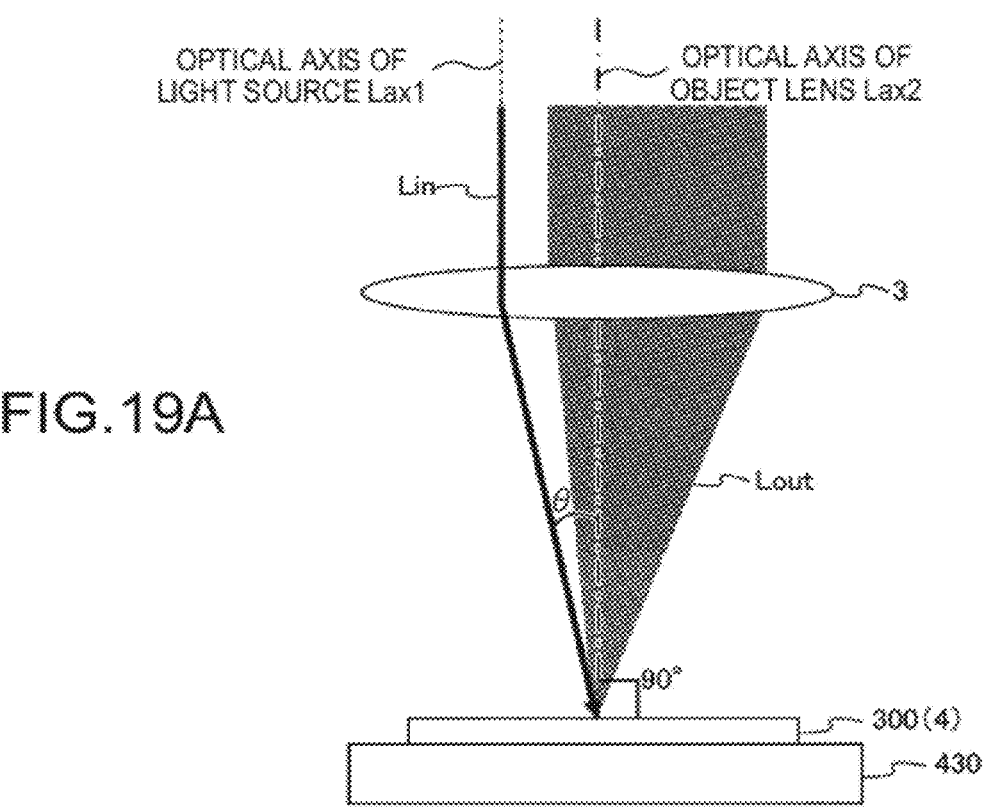
FIGS. 19A and 19B are explanatory diagrams illustrating a technique for introducing incident light into a sensor chip with an inclination.
Figure 19B:
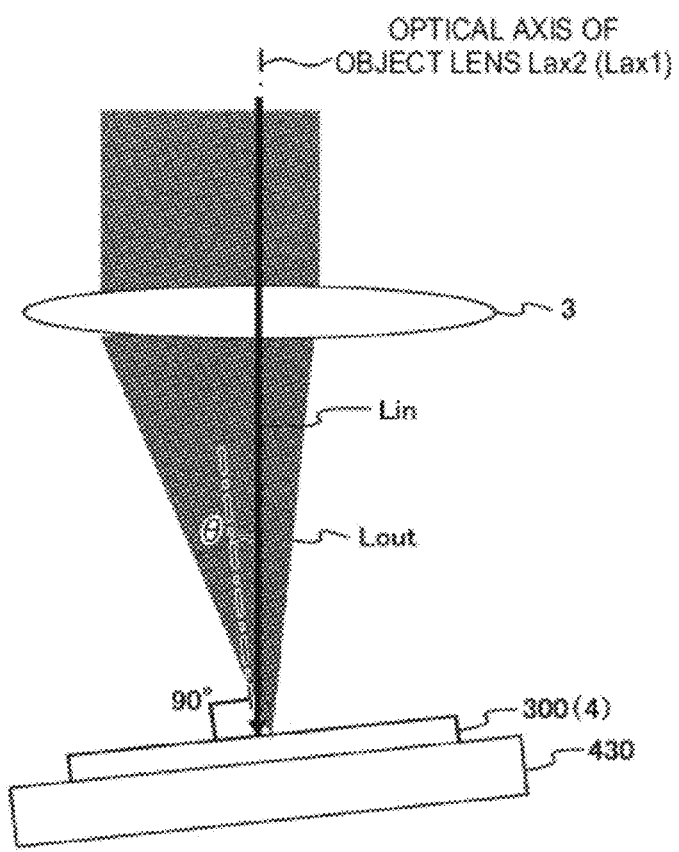

FIGS. 19A and 19B are explanatory diagrams illustrating a technique for introducing incident light into a sensor chip 300 with an inclination. Hereinafter, the like reference numerals denote like elements as in FIG. 1B, and description thereof will not be repeated. In the example in FIG. 19A, the incident light Lin is inclined with respect to the sensor chip 300 by deviating an optical axis Lax1 of a light source from an optical axis Lax2 of an object lens 3. In the example in FIG. 19B, the optical axis Lax1 of the light source matches with the optical axis Lax2 of the object lens 3, and the sensor chip 300 is inclined with respect to the optical axis Lax2 of the object lens 3 so that the incident light Lin is inclined with respect to the sensor chip 300.

In the example in FIG. 19A, the sensor chip 300 is disposed on the support 430 perpendicularly to the optical axis Lax2 of the object lens 3. In addition, the incident light Lin is incident to the object lens 3 in parallel to the optical axis Lax of the object lens 3 by separating the optical axis Lax1 of the single activated light source from the optical axis Lax2 of the object lens 3 in a predetermined distance. The predetermined distance is a distance at which the incident angle of the incident light Lin with respect to the sensor chip 300 becomes θ by refraction in the object lens 3. The light Lout from the sensor chip 300 is incident to the object lens 3 and guided to the half mirror 2 in FIGS. 1A to 1D by the object lens 3.

In the example in FIG. 19B, an angle between the normal line of the plane of the sensor chip 300 (the plane of the substrate 100) and the optical axis Lax2 of the object lens 3 is set to θ. In addition, the incident light Lin from the single activated light source is incident along the optical axis Lax2 of the object lens 3. Then, the incident light Lin is incident to the sensor chip 300 with an incident angle θ without being refracted by the object lens 3. In order to incline the sensor chip 300, as shown in FIG. 19B, the support 430 may be inclined. In addition, the support surface of the support 430 may be inclined by modifying the example in FIG. 19B.

2.7. Optical Device (Metal Nano-structure Using Deposition)

Figure 20A:
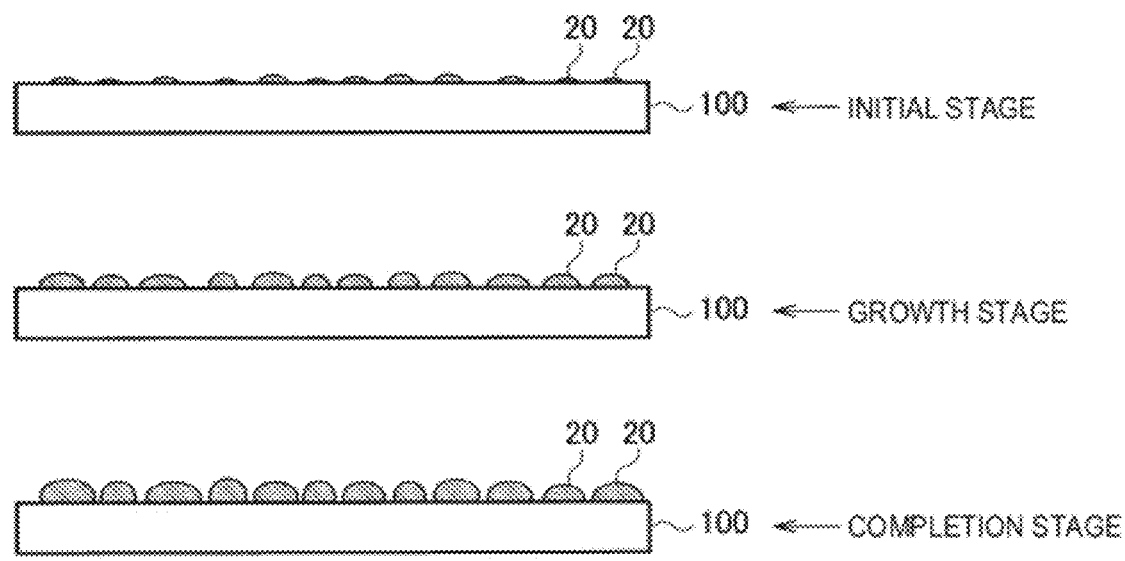
FIGS. 20A and 20B are schematic explanatory diagrams illustrating a method of manufacturing an electrical conductor.
Figure 20B:
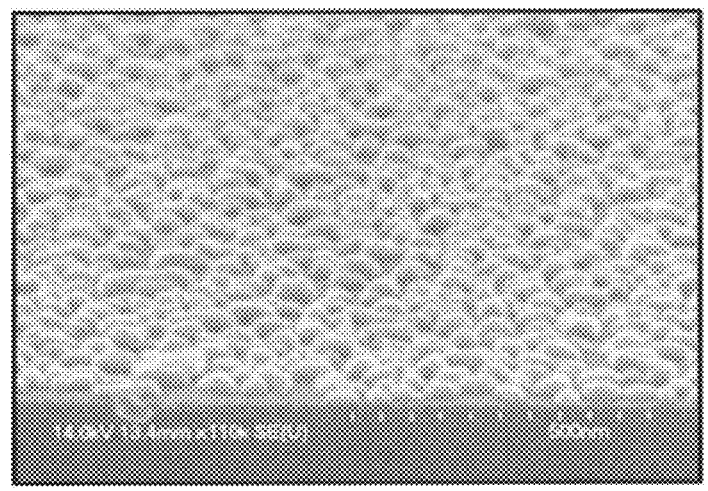

FIGS. 20A and 20B are schematic explanatory diagrams illustrating a method of manufacturing an electrical conductor. For example, a method of manufacturing a metal nano-structure using a photolithographic technique as shown in FIG. 8A is called a top-down technique, in which the metal nano-structure has a regular arrangement structure and also has a gap where an enhanced electric field is generated. In contrast, the metal nano-structure having an independent island shape formed through deposition has an irregular size or shape, and a gap where the enhanced electric field is generated is also irregular. That is, there is a place where the enhanced electric field is strong and a place where the enhanced electric field is weak, and a polarization direction of the incident light Lin also has freedom. However, since the metal nano-structure formed through deposition has a condition that a strong enhanced electric field is generated in some places, variations in the manufacturing can be advantageously absorbed.

For example, it is possible to manufacture a metal nano-structure through deposition using a vacuum deposition machine. As an exemplary deposition condition, borosilicate may be employed in the substrate 100. In addition, silver (Ag) may be employed as deposition metal, and the silver (Ag) may be heated and deposited on the substrate 100. In this case, the substrate 100 is not necessary to be heated, and the heating/deposition rate may be set to 0.03 to 0.05 nm/sec.

FIG. 20A schematically illustrates a process of forming an island. At the initial stage of the deposition island, a seed of silver (Ag) is formed on the substrate 100. At the growth stage of the deposition island, silver (Ag) is grown from the seed and increases in size. At the completion stage of the deposition island, while a distance between neighboring islands is reduced, the vacuum deposition may stop before the neighboring islands stick to each other.

In FIG. 20B, an electron microscope photograph of the metal nano-structure manufactured in practice is illustrated. In general, Ag islands of approximately 25 nm are formed such that each of them is isolated. If deposition is carried out further, the Ag islands are connected to each other, and finally, form a film. Typically, it is necessary to deposit the islands in a regular film shape. However, in this case, it is preferable that the independent Ag islands be narrowly formed with a high density as long as possible.

As the plane-polarized light is irradiated onto such a metal nano-structure, a strong enhanced electric field is formed in the vicinity of the gap between the deposition islands while the position or the direction of the gap is not constant. The thing contributing to the enhanced electric field is a P-polarized wave of the incident light Lin matching with the direction of the gap. A strong enhanced electric field may be formed by the polarization direction, or a slightly weak enhanced electric field may be formed.

2.8. Spectroscopic Analysis

Figure 21A:
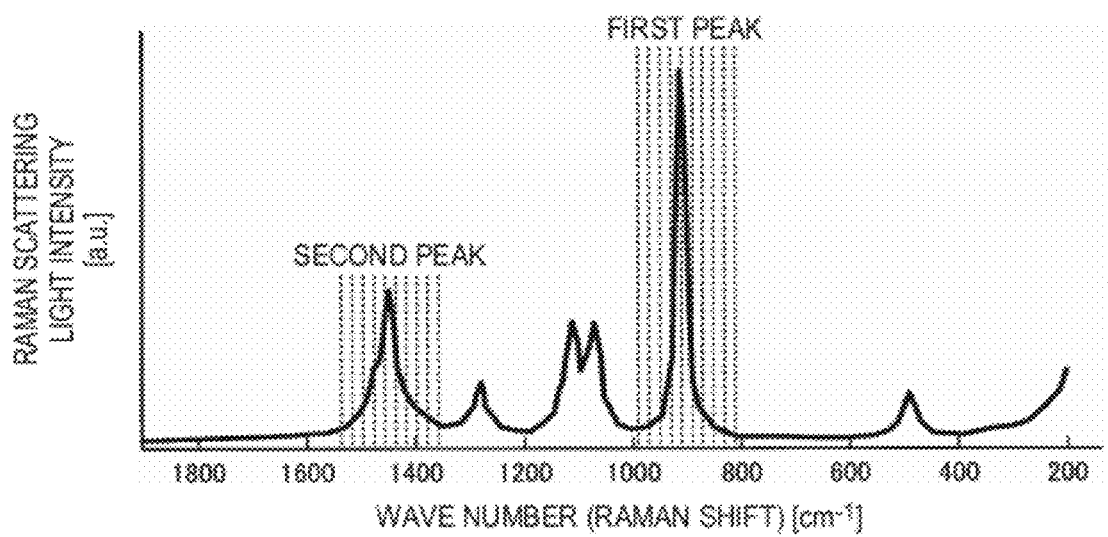
FIGS. 21A to 21C are schematic explanatory diagrams illustrating peak extraction from Raman spectra.
Figure 21B:
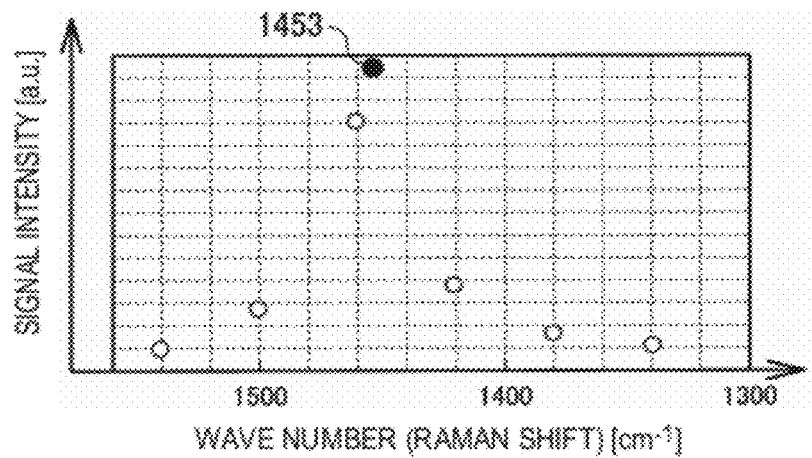
Figure 21C:
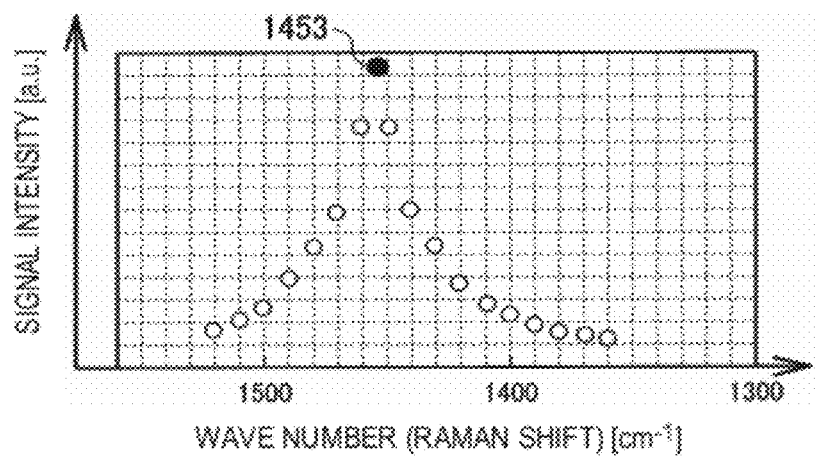

FIGS. 21A to 21C are schematic explanatory diagrams illustrating peak extraction of the Raman spectrum. FIG. 21A illustrates a Raman spectrum detected when excitation laser is irradiated onto a certain substance, in which the Raman shift is expressed using a wave number. In the example in FIG. 21A, it is recognized that a first peak (883 cm$^{-1}$) and a second peak (1453 cm$^{-1}$) are characteristic. By checking the obtained Raman spectrum against the data stored in advance (for example, checking the light intensity and the Raman shift of the first peak, and against the light intensity and the Raman shift of the second peak), it is possible to specify the target substance.

FIG. 21B illustrates a signal intensity (white circle) when a spectrum around the second peak is detected by the optical receiver element 380 using a spectroscopic element 370 having a low resolution (40 cm$^{-1}$). FIG. 21C illustrates a signal intensity (white circle) when a spectrum around the second peak is detected by the optical receiver element 380 using a spectroscopic element 370 having a high resolution (10 cm$^{-1}$). When the resolution is high such as 10 cm$^{-1}$, it becomes easy to accurately specify the Raman shift (black circle) of the second peak.

While the embodiments of the invention have been described in detail in the foregoing description, it will be appreciated by those skilled in the art that various modifications can be made without substantially departing from the novel matter and effects of the invention. Therefore, such various modifications are intended to be included in the scope of the invention. For example, through the description and the drawings, the terminologies referred to at least once together with other words which may be broader or have the same meaning may be substituted for other terms in any parts of the description or the drawings. In addition, configurations or operations of the optical device, the detection apparatus and the analysis apparatus may be variously modified without limitation to the embodiments of the invention.

The entire disclosure of Japanese Patent Application No. 2010-205510, filed Sep. 14, 2010 is expressly incorporated by reference herein.

What is claimed is:

1. An optical device unit detachable from a detection apparatus, the optical device unit comprising:
   an optical device having an electrical conductor, the optical device being capable of enhancing Raman scattering light generated by receiving light from a light source of the detection apparatus; and
   a first guide unit that guides a gaseous sample to the optical device, wherein
   the first guide unit has a first fluid path through which the gaseous sample flows from an import opening of the first fluid path to the optical device,
   the first fluid path is acutely bent one or more times, and the first fluid path has an inner surface that blocks an incident ray of external light and that has a light reflecting property.

2. The optical device unit according to claim 1, further comprising a filter for removing dust from inside the first fluid path,
wherein the filter blocks the external light.

3. The optical device unit according to claim 1, further comprising an identification code that can be read by the detection apparatus and identifies the optical device.

4. The optical device unit according to claim 1, wherein the first guide unit has a second fluid path connected to the first fluid path, and
the second fluid path rotates the gaseous sample in an area facing the optical device.

5. A detection apparatus comprising:
the optical device unit according to claim 1;
a second guide unit connectable to the first guide unit;
the light source;
a first optical system that enters the light from the light source into the electrical conductor of the optical device; and
a detector that detects Raman scattering light from the light scattered or reflected by the electrical conductor,
wherein the second guide unit guides the gaseous sample to an outlet.

6. The detection apparatus according to claim 5, wherein the electrical conductor of the optical device includes a first protrusion group having a plurality of protrusions,
each of the plurality of protrusions of the first protrusion group is arranged with a first period along a direction parallel to a conductor imaginary plane of the electrical conductor, and
the first optical system introduces the light from the light source into the first protrusion group such that a component parallel to a polarization imaginary plane of a polarization direction of the light from the light source is parallel to an arrangement direction of the first protrusion group.

7. The detection apparatus according to claim 6, wherein each of the plurality of the protrusions of the first protrusion group includes a second protrusion group formed of an electrical conductor on a front surface of the first protrusion group, and
each of a plurality of protrusions of the second protrusion group corresponding to any one of the plurality of protrusions of the first protrusion group is arranged with a second period shorter than the first period along a direction parallel to the virtual plane.

8. The detection apparatus according to claim 6, further comprising a third protrusion group formed of a third electrical conductor on a surface between neighboring protrusions of the first protrusion group on a surface where the first protrusion group is arranged,
wherein each of a plurality of protrusions of the third protrusion group is arranged with a third period shorter than the first period along the direction parallel to the virtual plane between the neighboring protrusions of the first protrusion group.

9. The detection apparatus according to claim 6, wherein surface plasmon resonance in the event that a propagating direction of the light from the light source is inclined with respect to a normal line directed to the virtual plane is generated in each of first and second resonance peak wavelengths,
a first resonance peak wavelength band having the first resonance peak wavelength has an excitation wavelength in surface-enhanced Raman scattering caused by the surface plasmon resonance, and
a second resonance peak wavelength band having the second resonance peak wavelength has a Raman scattering wavelength in the surface-enhanced Raman scattering.

10. The detection apparatus according to claim 5, further comprising a second optical system that guides the Raman scattering light to the detector,
wherein the detector receives the Raman scattering light through the second optical system.

* * * * *